US008927260B2

(12) United States Patent
Chin et al.

(10) Patent No.: US 8,927,260 B2
(45) Date of Patent: Jan. 6, 2015

(54) ANAYLTE DETECTION SYSTEM USING AN OSCILLATING MAGNETIC FIELD

(75) Inventors: Robert C. Chin, Austin, TX (US); Ronald E. Ham, Austin, TX (US)

(73) Assignee: Fabrico Technology, Inc., Austin, TX (US)

( * ) Notice: Subject to any disclaimer, the term of this patent is extended or adjusted under 35 U.S.C. 154(b) by 321 days.

(21) Appl. No.: 13/024,227

(22) Filed: Feb. 9, 2011

(65) Prior Publication Data

US 2011/0194979 A1   Aug. 11, 2011

Related U.S. Application Data

(63) Continuation-in-part of application No. 12/046,964, filed on Mar. 12, 2008, now Pat. No. 8,026,071.

(60) Provisional application No. 61/302,718, filed on Feb. 9, 2009, provisional application No. 60/894,371, filed on Mar. 12, 2007.

(51) Int. Cl.
*G01N 33/553* (2006.01)
*G01N 33/543* (2006.01)
*G01N 33/58* (2006.01)

(52) U.S. Cl.
CPC .......... *G01N 33/54326* (2013.01); *G01N 33/58* (2013.01)
USPC ....................................... 435/287.2; 436/526

(58) Field of Classification Search
None
See application file for complete search history.

(56) References Cited

U.S. PATENT DOCUMENTS

| | | | | | |
|---|---|---|---|---|---|
| 3,473,110 | A | * | 10/1969 | Hardin et al. | 324/236 |
| 4,276,514 | A | * | 6/1981 | Huang | 330/149 |
| 4,709,205 | A | * | 11/1987 | Baurand et al. | 324/127 |
| 4,916,081 | A | | 4/1990 | Kamada et al. | |
| 5,055,408 | A | | 10/1991 | Higo et al. | |
| 5,123,901 | A | | 6/1992 | Carew | |

(Continued)

FOREIGN PATENT DOCUMENTS

| | | | |
|---|---|---|---|
| EP | 1036328 B1 * | 10/2004 | |
| WO | WO 9625791 A1 * | 8/1996 | H03F 1/32 |

(Continued)

OTHER PUBLICATIONS

Makiranta, et al., Modeling and Simulation of Magnetic Nanoparticle Sensor, Proceedings of the 2005 IEEE, Engineering in Medicine and Biology 27th Annual Conference, 2005.*

(Continued)

*Primary Examiner* — Chris L Chin
*Assistant Examiner* — Richard Moerschell
(74) *Attorney, Agent, or Firm* — Larson, Newman, LLP

(57) ABSTRACT

An analyte detection system includes a detector situated close to a well of a substrate. The well includes conjugated paramagnetic beads. The detection system also includes a magnetic field generator that provides an oscillating magnetic field in the well and the detector, an oscillator circuit coupled to the detector, and a circuit coupled to the detector that detect the conjugated paramagnetic beads. A method includes applying a magnetic field to well of a substrate with conjugated paramagnetic beads, alternating the polarity of the magnetic field, detecting a waveform associated with the alternating magnetic field, and associating the waveform with the quantity of conjugated paramagnetic beads. An analyte detection kit includes a substrate with an attached antibody that is reactive to the analyte, a conjugated paramagnetic particle, and a conjugated paramagnetic particle detector.

19 Claims, 9 Drawing Sheets

(56) References Cited

U.S. PATENT DOCUMENTS

| | | | |
|---|---|---|---|
| 5,182,479 A * | 1/1993 | Behagel et al. | 327/379 |
| 5,343,168 A * | 8/1994 | Guthrie | 331/16 |
| 5,374,395 A | 12/1994 | Robinson et al. | |
| 5,445,970 A * | 8/1995 | Rohr | 436/526 |
| 5,445,971 A * | 8/1995 | Rohr | 436/526 |
| 5,567,588 A | 10/1996 | Gold et al. | |
| 5,698,450 A | 12/1997 | Ringrose et al. | |
| 5,981,297 A | 11/1999 | Baselt | |
| 5,998,224 A * | 12/1999 | Rohr et al. | 436/526 |
| 6,046,585 A * | 4/2000 | Simmonds | 324/239 |
| 6,133,043 A | 10/2000 | Talley et al. | |
| 6,582,381 B1 | 6/2003 | Yehezkeli et al. | |
| 6,661,286 B2 * | 12/2003 | Filoramo et al. | 330/254 |
| 6,939,677 B1 | 9/2005 | Ceriani et al. | |
| 6,969,865 B2 * | 11/2005 | Duchon et al. | 250/573 |
| 2001/0008760 A1 | 7/2001 | King et al. | |
| 2004/0086918 A1 | 5/2004 | Lowey et al. | |
| 2004/0153879 A1 * | 8/2004 | Fukutani et al. | 714/48 |
| 2006/0194327 A1 * | 8/2006 | Kahlan et al. | 436/86 |
| 2008/0160630 A1 * | 7/2008 | Liu et al. | 436/164 |
| 2010/0006439 A1 * | 1/2010 | Ham et al. | 204/547 |

FOREIGN PATENT DOCUMENTS

| | | | | |
|---|---|---|---|---|
| WO | 2004/053490 A1 | 6/2004 | | |
| WO | 2005/015216 A1 | 2/2005 | | |
| WO | WO 2007105141 A2 * | 9/2007 | | G01R 33/02 |

OTHER PUBLICATIONS

Jovanovic et al., A CMOS Voltage Controlled Ring Oscillator with Improved Frequency Stability, Scientific Publications of the State University of Novi Pazar, Ser. A: Appl. Math. Inform. And Mech. 2(1): 2010, 1-9.*

Hajimiri et al., Jitter and Phase Noise in Ring Oscillators, IEEE Journal of Solid State Circuits, 34(6), 1999, 790-804.*

Bowtell, David D. L.; "Options Available—from Start to Finish—for Obtaining Expression Data by Microarray," Nature America Inc.; vol. 21 (Jan. 1999) (8 pages).

Kriz, C.B., et al; "Magnetic Permeability Measurements in Bioanalysis and Biosensors," Analytical Chemistry 1996, 68, 1966-1970; (5 pages).

Carulli, J., et al; "High Throughput Analysis of Differential Gene Expression," Journal of Cellular Biochemistry Supplements 30/31; 286-296 (1998) (11 pages).

Current Patents Gazette; Thomson, Issue 0520, May 20, 2005, (2 pages).

Drolet, D., et al; "An Enzyme-Linked Oligonucleotide Assay," Nature Biotechnology, vol. 14, Aug. 1996; (5 pages).

Enpuku, K., et al; "Detection of Magnetic Nanoparticles with Superconducting Quantum Interference Device (SQUID) Magnetometer and Application to Immunoassays," Jpn. J. Appl. Phys., vol. 38 (1999) pp. L1102-L1105; (4 pages).

Keller, W., et al; "Degradation of DNA RNA Hybrids by Ribonuclease H and DNA Polymerases of Cellular and Viral Origin," Proc. Nat. Acad. Sci. USA; vol. 69, No. 11, pp. 3360-3364, Nov. 1972 (5 pages).

Kriz, K., et al; "Advancements Toward Magneto Immunoassays," Elsevier, Biosensors & Bioelectronics 13 (1998) pp. 817-823 (7 pages).

Luxton, R. et al; "Use of External Magnetic Fields to Reduce Reaction Times in an Immunoassay Using Micrometer-Sized Paramagnetic Particles as Labels (Magnetoimmunoassay)," Analytical Chemistry, vol. 76, No. 6, Mar. 15, 2004 pp. 1715-1719 (5 pages).

Pathak, R., et al; "Subtractive Differential Display: a Modified Differential Display Technique for Isolating Differentially Expressed Genes," Molecular Biology Rep. (2007) vol. 34; pp. 41-46 (6 pages).

Richardson, J., et al; "A Novel Measuring System for the Determination of Paramagnetic Particle Labels for use in Magneto-Immunoassays," Elsevier, Biosensors & Bioelectronics 16 (2001) pp. 1127-1132 (6 pages).

Stein, J., et al; "Differential Display Technology: a General Guide," CMLS Cellular and Molecular Life Sciences, vol. 59 (2002) pp. 1235-1240 (6 pages).

Richardson, J., et al; "The Use of Coated Paramagnetic Particles as a Physical Label in a Magneto-Immunoassay," Elsevier, Biosensors & Bioelectronics 16 (2001) pp. 989-993 (5 pages).

Final Office Action mailed Dec. 17, 2010 for U.S. Appl. No. 12/046,964, 16 pages.

Non-Final Office Action mailed Jul. 2, 2010 for U.S. Appl. No. 12/046,964, 8 pages.

* cited by examiner

ANAYLTE DETECTION SYSTEM USING AN OSCILLATING MAGNETIC FIELD

CROSS-REFERENCE TO RELATED APPLICATIONAPPLICATIONS

The present application claims priority from U.S. Provisional Patent Application No. 61/302,718, filed Feb. 9, 2010, entitled "SYSTEMS AND METHODS FOR DETECTING TARGET ANALYTES," naming inventors Robert C. Chin and Ronald E. Ham, which application is incorporated by reference herein in its entirety.

The present application is a continuation-in-part of U.S. patent application Ser. No. 12/046,964, filed Mar. 12, 2008, entitled "SYSTEMS AND METHODS FOR DETECTING TARGET ANALYTES," naming inventors Robert C. Chin and Gregory F. Lopreato, which claims priority to U.S. Provisional Patent Application No. 60/894,371, filed Mar. 12, 2007, entitled "SYSTEMS AND METHODS FOR DETECTING TARGET ANALYTES," naming inventors Robert C. Chin and Gregory F. Lopreato.

FEDERAL FUNDING

The U.S. government has a paid-up license in this invention and the right in limited circumstances to require the patent owner to license others on reasonable terms as provided for by the terms of FA8650-06-C-6646 awarded by USAF/AFMC Air Force Research Laboratory.

FIELD OF THE DISCLOSURE

This disclosure, in general, relates to systems and method for detecting target analytes.

BACKGROUND

Increasingly, industry is seeking detection methods for low concentration analytes. From detection of early stages of disease to early warning of chemical and biological hazards, detection of analytes increasingly is becoming of concern to society.

In particular, medical diagnostic end users are seeking to detect viral infections, such as HIV, at earlier stages. Early stage detection leads to treatment when a disease is manageable. For example, anti-viral medications have shown increased efficacy, possibly to the point of curing infected HIV patients when administered early. In other examples, early detection of avian influenza can lead to improved treatment of patients and prevention of epidemics.

In another example, militaries and civil defense agencies are seeking early warning and detection systems for chemical and biological agents. With increased threat of terrorism and rogue governments, concern about chemical or biological attacks has grown. Detection of analytes and residue relating to such agents can lead to improved security and faster response, ultimately saving lives.

Further, analyte detection is useful in research. Industry is seeking to automate and miniaturize laboratory assay equipment, leading to a desire for detection methods that are sensitive and can be performed with small quantities. However, traditional methods are often expensive and inefficient. For example, gas chromatography and mass spectrometry use large cumbersome equipment that is expensive to maintain. In other exemplary methods, such as test strips and titration, the output is less sensitive to reagents and analytes. In addition, such methods, while convenient, are inaccurate and often, subjective. For biological samples, culture methods are time consuming and use expert training to achieve results. In particular, DNA testing through gel electrophoresis is time consuming and utilizes a large quantity of DNA. While the DNA can be replicated to produce the quantity used in testing, such replication adds time to the testing process.

As such, an improved method of detecting analytes would be desirable.

BRIEF DESCRIPTION OF THE DRAWINGS

The present disclosure may be better understood, and its numerous features and advantages made apparent to those skilled in the art by referencing the accompanying drawings.

DESCRIPTION OF THE EMBODIMENTS

In a particular embodiment, a detection system includes a sensor, an oscillator circuitry connected to the sensor, and analysis circuitry connected to the oscillator circuitry. In an example, the sensor forms an inductive component of the oscillator circuitry. The sensor can be disposed in proximity to a specimen exposed to a time varying magnetic field. The time varying magnetic field forces a paramagnetic specimen to go from a saturated to a non-saturated state. This phenomenon is caused by the fact that the paramagnetic specimens' magnetic permeability ($\mu$) is time-variant. This forced state of saturation to non-saturation causes a change in the inductance of the sensor and an output of the sensor. The sensor output can influence the resonant frequency of the oscillator circuitry, and the resulting changes in an oscillator output signal can be analyzed to determine features of the specimen. For example, the oscillator output signal can be demodulated and analysis performed on the magnitude of frequency components of Bessel sidebands. In another example, frequency shift or phase shift can be analyzed.

In an exemplary embodiment, the specimen includes a quantity of conjugated paramagnetic particles. Measuring a specimen includes subjecting a specimen to an alternating magnetic field. The peak magnetic field can be strong enough to magnetically saturate conjugated paramagnetic particles that are directly or indirectly reactive to a target analyte. The induced time-variance of the magnetic permeability of the particles can change the inductance of a detector inductor that is part of an oscillator circuit. The changes in the detector inductor can cause the oscillation frequency of the oscillator circuit to change. A characteristic of the changing oscillation frequency can be associated with a quantity of the conjugated paramagnetic particles, and hence with a quantity of the target analyte. An exemplary characteristic includes a change in a magnitude of a frequency component of the Bessel sideband of the output from the oscillator circuitry.

Figure 1:
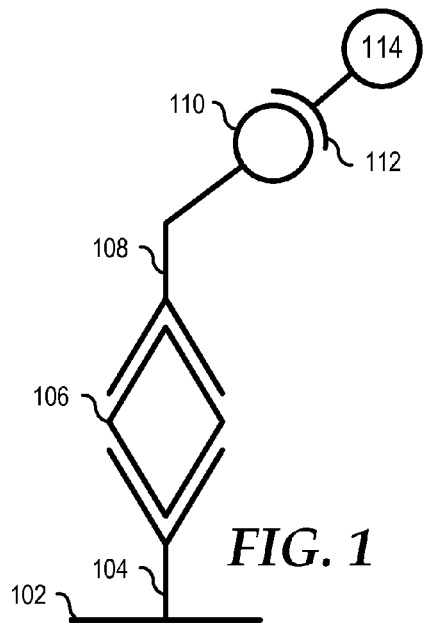
FIGS. 1, 2a, 2b, and 2c include illustrations of exemplary assays to detect target analytes using conjugated paramagnetic particles.

FIG. 1 includes a diagram illustrating an exemplary assay to detect a target analyte 106. In an exemplary embodiment, a substrate 102 includes a receptor 104. For example, the substrate 102 can include a polymeric material or a ceramic material, such as glass. In another example, the substrate 102 includes a semiconductor material. In a further example, the substrate is a well of a multi-well plate.

The receptor 104 can bind the target analyte 106. For example, a portion of the target analyte 106 can bond to a portion of the receptor 104. Further, a receptor 108 can bind to the target analyte 106. For example, a portion of the receptor 108 can bind to a portion of the target analyte 106. In an exemplary embodiment, the receptor 108 includes a characteristic site 110, such as a conjugated biotin or a distal protein chain. A conjugated paramagnetic particle 114 can include a receptor 112 adapted to bind to the characteristic site 110 of the receptor 108. For example, an anti-biotin antibody conjugated to the conjugated paramagnetic particle 114 can bind to a biotin attached to the receptor 108.

In an exemplary embodiment, the amount of the target analyte 106 can be determined from the amount of conjugated paramagnetic particles 114 associated with the substrate. For example, a solution including conjugated paramagnetic particles 114 can be washed over the substrate 102 after the substrate 102 has been exposed to a solution suspected of including the target analyte 106 and after the substrate 102 has been exposed to the receptor 108. After washing and optionally drying, the number of paramagnetic particles 114 remaining in proximity to the substrate 102 are correlated with the amount of target analyte 106 in the solution suspected of having the target analyte 106. Such paramagnetic particles 114 can be detected using, for example, an induction coil or antenna coupled to a detection circuitry. In a particular embodiment, such paramagnetic particles 114 can be detected by a detector inductor that is part of an oscillator circuit. An alternating magnetic field can be applied to the specimen, resulting in an induced change in a frequency component of a signal from the oscillator circuit. A characteristic of the changing frequency component can be associated with the quantity of the paramagnetic particles 114.

In an exemplary embodiment, a receptor includes a chemical structure adapted to respond to the target. In a particular example, the receptor includes sites that bind with one or more sites located on the target. In an example, the receptor is non-specific and can bind to more than one type of target. For example, the receptor can bind to many targets of different types. In an example, a non-specific receptor can bind to many proteins of a particular animal or plant species, such as human, any one of the apes, any one of the rodents, or any one of the avian species. Alternatively, the receptor can be specific and can bind to a specific target, exclusive of other targets. For example, the receptor can bind to a specific antigen, such as a particular virus, a particular chemical, or a particular protein.

In a particular embodiment, the receptor can be formed from an antibody, a protein, or a nucleic acid sequence. In an example, the receptor can include an antibody. For example, a tissue sample or a target substance can be introduced into an animal subject that forms antibodies to aspects of the tissue sample or the target substance. Such antibodies can be isolated and prepared for use as receptors. An antibody can bind specifically to a particular virus, a particular metabolite, a particular protein, a particular drug, or a particular chemical or biological warfare agent. In an alternative example, the receptor can be an antigen useful in detecting an antibody.

Depending on the nature of the target analyte, an animal system can be selected to enhance the detection method. For example, the target analyte can be injected into a selected animal system to develop a receptor, such as an antibody. Based on the selected animal system, a paramagnetic particle can be conjugated to an antibody selective for the proteins of the selected species of animal. For example, the animal system can be selected from an avian species, such as a goose, a chicken, a duck, a swan, or a wild bird species. In another example, the animal system can be selected from a greater ape species, such as an orangutan, a gibbon, a siamang, a gorilla, a chimpanzee, or a bonobo, or from a monkey, such as a rhesus, a macaque, a baboon, a vervet, a squirrel monkey, an owl monkey, a tamarin, or a marmoset. In a further example, the antibody can be a human antibody. In a particular embodiment, the antibody can be formed in a traditional system, such as a rodent, rabbit, goat, or horse. As such, the paramagnetic particle can be conjugated to a corresponding antibody responsive to proteins of the selected animal species, such as an anti-orangutan, an anti-chimpanzee, an anti-tamarin, an anti-chicken, or an anti-goose antibody. In an alternative embodiment, the receptor is biotinylated and the paramagnetic particle is conjugated to an anti-biotin receptor. An exemplary anti-biotin receptor includes avidin or streptavidin. Alternatively, the anti-biotin receptor can be an anti-biotin antibody, which can have particular advantage in more specific binding to biotinylated antibody type receptors.

In another example, the receptor can be a nucleic acid sequence, such as a DNA or an RNA sequence. In a particular example, the nucleic acid sequence forms a strand of oligonucleotides, often referred to as an aptamer that can bind to a specific target. In an embodiment, an aptamer can be selected that binds to a specific target, such as a chemical species. For example, an aptamer can be selected that binds to a chemical or biological warfare agent. In another example, an aptamer can be selected to bind to residues of drugs and explosives. In particular, aptamers can be small and can be particularly suited to bind to small molecules. In a further example, an aptamer can be selected to bind to a particular sequence of DNA or RNA.

In an exemplary embodiment, the receptors can be bonded or coupled to the surface of the substrate. In another example, the receptors can be conjugated to a paramagnetic particle. In a further example, the receptor can be biotinylated or can be used as a layer of a multi-layer detection protocol.

A conjugated paramagnetic particle is a particle formed of a paramagnetic material on the surface of which a conjugated molecule is bound. In an example, the paramagnetic particle includes a polymer binder or coating and a paramagnetic material disposed in the polymer. For example, the paramagnetic particle can include a paramagnetic ceramic material. In a particular example, the paramagnetic particle includes hematite or a blend of hematite and ferrite. The conjugated molecule can be reactive to bind with particular molecules, such as proteins, nucleic acid sequences, or small molecule chemicals.

The target is generally an analyte to be detected. For example, the target can be an in vivo endogenous target derived from a tissue or fluid sample of a species and in particular, can be an antigen. In an example, the endogenous target can be derived from a fluid, such as blood, plasma, serum, urine, sweat, tears, saliva, ejaculate, or from a tissue, bone, or hair. The endogenous target, for example, can be a protein, such as a protein expressed by a subject. A particular example includes a prion. In a further example, the endogenous target can be a metabolite indicative of a disease. In an additional example, the endogenous target can be toxic metabolite derived from a biological source. In a further example, the endogenous target can include a sequence of DNA or RNA. Alternatively, the target can be an in vivo exogenous target, such as a virus or bacteria. An exemplary exogenous target can include a virus, such as a human immunodeficiency virus (HIV), an influenza virus such as H5N1, a cold virus, or a hepatitis virus. In another example, the exogenous target can include a biological warfare agent when derived from bodily fluid or tissue. Such a biological warfare agent can include anthrax, brucellosis, cholera, Congo-Crimean hemorrhagic fever, Ebola hemorrhagic fever, melioidosis, plague, Q-fever, rift valley fever, smallpox, tularemia, Venezuelan equine encephalitis, ricin, saxitoxin, staphylococcal enterotoxin B, clostribium perfringens toxin, botulinum toxin, or trichothecene mycotoxin.

Alternatively, the target can be an ex vivo target and can be derived from an environmental source. For example, the target can be derived from water, such as water derived from an ocean, sea, lake or tributary, rainwater, dew, or potable water supplies. In another example, the exogenous target can be derived from air, soil, or rock.

In a particular embodiment, an ex vivo target can include a drug, a chemical warfare agent, an explosive, or a residue thereof. An exemplary drug can include cocaine, methamphetamine, heroin, marijuana, or LSD. An exemplary warfare agent can include Somin, Sarin, VX, Tabu, nerve gas, or any combination thereof. An exemplary explosive can include TNT, thermite, thermate, nitroglycerin, gunpowder, Semtex, RDX, PETN, HMX, TETRYL, AMATOL, ANFO, COMP A-3, COMP B-3, COMP C-4, or any combination thereof. For example, an exemplary explosive residue target can include acetic anhydride, acetone, alcohol, ammonia, ammonium nitrate, aniline, azides, camphor, coal tar, diatomaceous earth, diazo compounds, fulminates, glycerol, guano, guncotton, nitric acid, nitroglycerin, phenol, potassium nitrate, saltpeter, transuranium elements, urea, or any combination thereof.

Figure 2A:
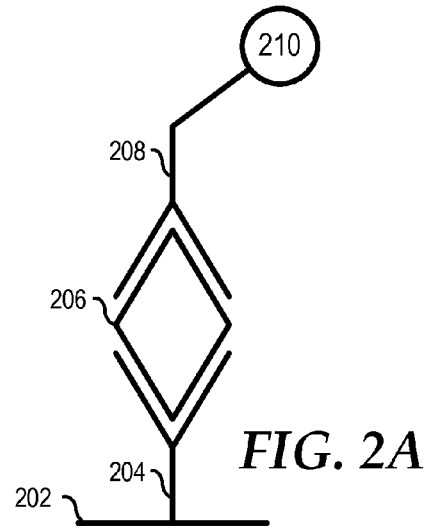

As illustrated in FIG. 1, the target analyte can be bound between two receptors and a conjugated paramagnetic particle, can bind to a distal end of one of the receptors. Alternatively, the target analyte can be bound to a receptor included on the substrate and a conjugated paramagnetic particle can bind to the target analyte. FIG. 2a includes a diagram illustrating an exemplary assay to detect a target analyte 206. In the exemplary embodiment, a substrate 202 is attached to a receptor 204. The receptor 204 can bind the target analyte 206. Further, a receptor 208 can bind the target analyte 206. In an exemplary embodiment, the receptor 208 is conjugated to a paramagnetic particle 210. In an example, the amount of the target analyte 206 can be determined from the number of conjugated paramagnetic particles 210 associated with the substrate.

Figure 2B:
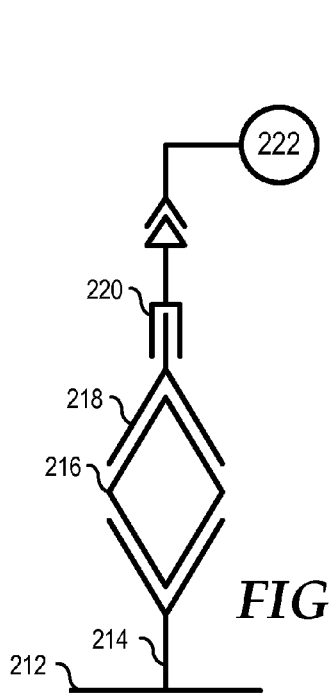

In alternative embodiments, multiple layers of receptors can be used to bind the conjugated paramagnetic particle to the target analyte. For example, FIG. 2b includes an illustration of a substrate 212 including a receptor 214. The receptor 214 can bind to a target analyte 216. A second receptor 218 can bind to the target analyte 216. In addition, a third receptor 220 can bind to a site on the second receptor 218 and a receptor conjugated to the paramagnetic particle 222 can bind to the third receptor 220.

Figure 2C:
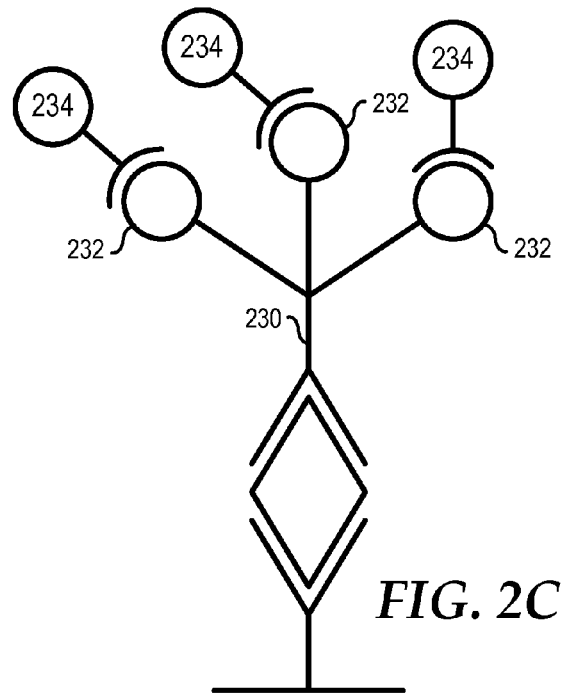

In a further example, the receptor can include more than one characteristic site to which a further receptor or conjugated paramagnetic particle can bind. For example, the receptor can be biotinylated with more than one biotin molecule and more than one anti-biotin conjugated paramagnetic particle can bind to the receptor. For example, FIG. 2c includes an illustration of a receptor 230 including more than one characteristic site 232 bonded to a conjugated paramagnetic particle 234.

Figure 3:
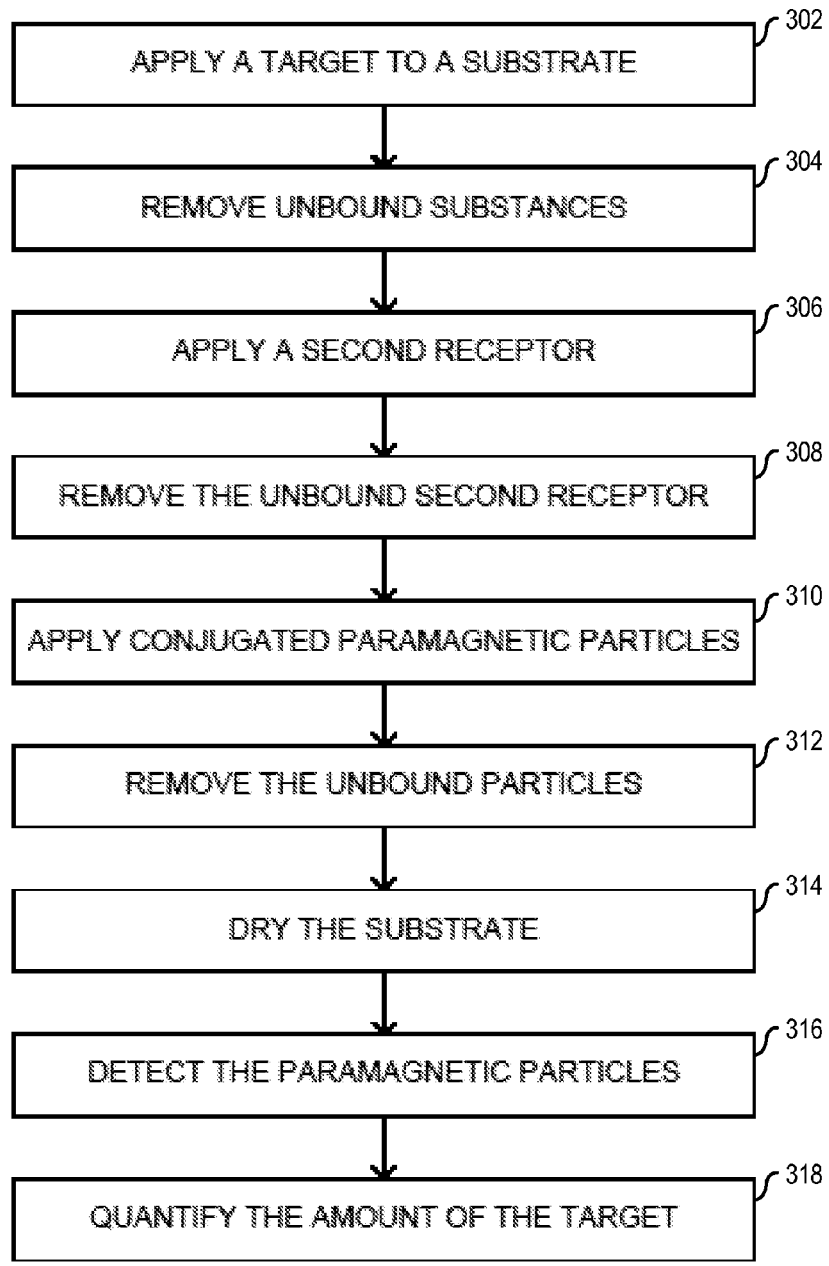
FIGS. 3 and 4 include flow diagrams illustrating methods of detecting target analytes using conjugated paramagnetic particles.

FIG. 3 is a flow diagram illustrating a method of detecting a target analyte using conjugated paramagnetic particles. In an exemplary embodiment, a target analyte or a solution suspected of including the target analyte is applied to or contacted with a substrate, as illustrated at 302. The substrate can include a receptor bound to the substrate. The receptor, for example, can be responsive to the target analyte. In particular, the receptor can specifically bind to the target analyte. In an exemplary embodiment, the substrate is a well of a multi-well plate. In an alternative example, the substrate can be a substrate of a semiconductor component.

In an exemplary embodiment, unbound substances are removed from the substrate, as illustrated at 304. For example, the unbound substances can be removed from the substrate by rinsing the substrate. In an example, the substrate can be rinsed with water, an aqueous solution, a solvent, or any combination thereof.

A second receptor, such as an antibody, can be applied to the substrate, as illustrated at 306. For example, the second receptor can be included in a solution that is contacted with the substrate. The second receptor can bind to the target analyte. Optionally, unbound second receptors can be removed from the substrate, as illustrated at 308. In an exemplary embodiment, the unbound antibody can be removed by rinsing the substrate. For example, the substrate can be rinsed with water, an aqueous solution, a solvent, or any combination thereof.

In an exemplary embodiment, conjugated paramagnetic particles can be applied to the substrate, as illustrated at 310. For example, the conjugated paramagnetic particles can be included in a solution that is contacted with the substrate. The conjugated paramagnetic particles can bind the second receptor. In an exemplary embodiment, the second receptor is conjugated to biotin and the conjugated paramagnetic particle is an anti-biotin conjugated paramagnetic particle. Further, the anti-biotin conjugated paramagnetic particle can be an anti-biotin antibody conjugated paramagnetic particle.

Unbound conjugated paramagnetic particles can be removed from the substrate, as illustrated at 312. For example, the unbound conjugated paramagnetic particles can be removed by rinsing the substrate, such as with water, an aqueous solution, a solvent, or any combination thereof. Bound conjugated paramagnetic particles can remain in proximity to the substrate.

While applying the target analyte to the substrate, applying the second receptor to the substrate, and applying the conjugated paramagnetic particles to the substrate are illustrated separately, the target, the second receptor, or the conjugated paramagnetic particle can be applied in combination. For example, the second receptor and the conjugated paramagnetic particles can be applied to the substrate concurrently. In another example, the target analyte, the second receptor, and the conjugated paramagnetic particles can be applied to the substrate concurrently.

Optionally, the substrate can be dried, as illustrated at 314. In an exemplary embodiment, the substrate is dried by exposing the substrate to air for a period of time sufficient to remove excess moisture. In an alternative embodiment, the substrate can be dried under vacuum, and in particular, can be lyophilized.

In an exemplary embodiment, the conjugated paramagnetic particles associated with the substrate are detected, as illustrated at 316. In an example, the amount of the conjugated paramagnetic particles associated with the substrate is determined by an analyte detection system. For example, conjugated paramagnetic particles can be perturbed in an alternating magnetic field and can change a characteristic of an oscillator signal (e.g., a frequency component of a sideband) of an oscillator circuitry connected to a sensor exposed to the alternating magnetic field. A greater change in a characteristic of the oscillator signal indicates a greater number of paramagnetic particles in proximity to the substrate.

The target analyte can be quantified, as illustrated at 318. In an exemplary embodiment, the quantification of the antigenic substance is based on the amount of paramagnetic particles associated with the substrate. In particular, the perturbation associated with the presence of paramagnetic particles can be correlated to a quantity or concentration of the target analyte. For example, the paramagnetic particle can be subjected to an alternating magnetic field that causes a change in an inductance of a detector inductor. The change in the detector inductor can cause a frequency component of a signal from an oscillator circuit to change. The change in the frequency component can be directly detected at an output of the oscillator circuit. In another embodiment, the frequency component can be detected at the output of the oscillator circuit as a change in phase, as a frequency shift of a signal, as an amplitude or magnitude of a particular harmonic, or a combination thereof.

Figure 4:
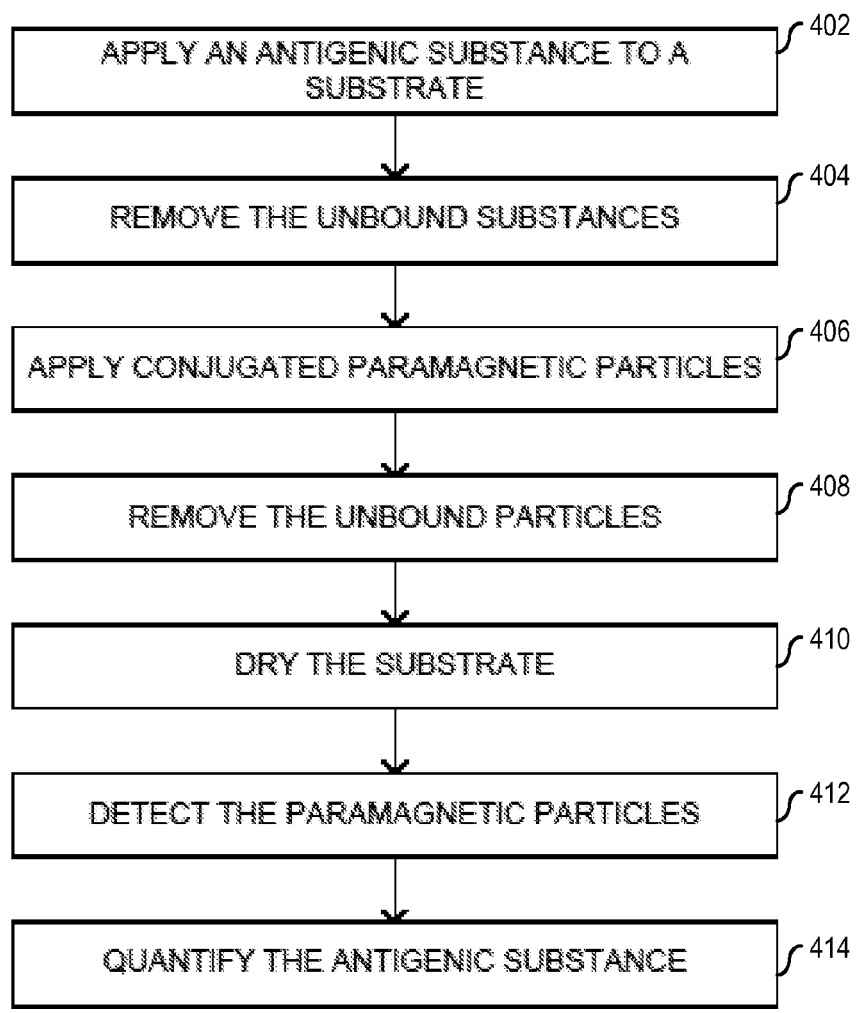

Optionally, the paramagnetic particles can be conjugated to a receptor that is responsive to the target analyte. In such an example, the second receptor is superfluous. In an exemplary embodiment, FIG. 4 includes a flow diagram illustrating a method of detecting an antigenic substance using conjugated paramagnetic particles. In an exemplary embodiment, an antigenic substance is contacted with a substrate, as illustrated at 402. The substrate, for example, can be a well of a multi-well plate. Alternatively, the substrate can be a substrate of a semiconductor device. Further, the substrate can include a first antibody attached to the surface of the substrate. The first antibody can be reactive to the antigenic substance.

In an exemplary embodiment, unbound substances are removed from the substrate, as illustrated at 404. For example, the unbound substances can be removed from the substrate by rinsing the substrate.

Conjugated paramagnetic particles can be applied to the substrate, as illustrated at 406. The conjugated paramagnetic particles can be conjugated to a molecule that can bind to the antigenic substance. In an exemplary embodiment, the conjugated paramagnetic particle is conjugated to an antibody reactive to the antigenic substance. Unbound conjugated paramagnetic particles can be removed from the substrate, as illustrated at 408. For example, the unbound conjugated paramagnetic particles can be removed by rinsing the substrate. Optionally, the substrate can be dried, as illustrated at 410. In an exemplary embodiment, the substrate can be dried by exposing the substrate to air for a period of time sufficient to remove excess moisture or can be dried under vacuum.

In an exemplary embodiment, the conjugated paramagnetic particles associated with the substrate are detected, as illustrated at 412. For example, the amount of the conjugated paramagnetic particles associated with the substrate can be determined using an analyte detection system. In particular, the number of paramagnetic particles remaining in proximity to the substrate can influence an inductance of a sensor. The number of paramagnetic particles can be correlated with the detected influence on the sensor.

Based at least in part on the detection of the paramagnetic particles, the presence of antigenic substance can be quantified, as illustrated at 414. For example, a correlation between the amount of antigenic substance and the amount of paramagnetic particles associated with the substrate or the detected influence of the paramagnetic particles on an electromagnetic field can be used to determine the amount of antigenic substance. While the method illustrated in FIG. 4 relates to antigenic substances, the method can also be implemented for other target analytes, and in particular, an ex vivo target analyte.

Figure 5:
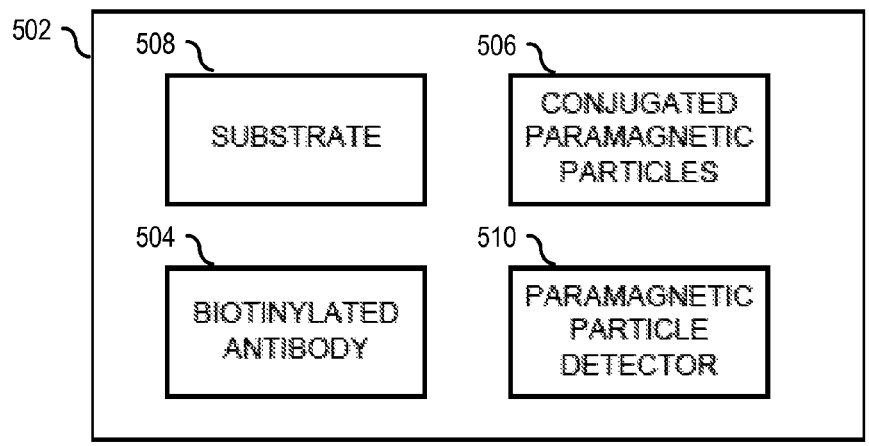
FIGS. 5 and 6 include block diagrams illustrating exemplary detection kits.

To implement the methods described above in relation to FIG. 3 and FIG. 4, a kit can be provided that includes the substrate and the conjugated paramagnetic particles. For example, FIG. 5 includes a block diagram illustrating an exemplary analyte detection kit 502. In an exemplary embodiment, the analyte detection kit 502 includes receptors 504, a conjugated paramagnetic particle 506, a substrate 508, and optionally, a paramagnetic particle detector 510. The substrate 508 can include a receptor bound to the surface of the substrate and reactive or responsive to an intended target analyte. In an exemplary embodiment, the substrate 508 is a multi-well plate. For example, the substrate 508 can include at least 2 wells, such as at least 4 wells. In a particular example, the substrate 508 includes at least 48 wells, such as at least 96 wells, or even, at least 384 wells.

The receptor 504 can be reactive to the intended target analyte. For example, the receptor 504 can bind to the intended target analyte. In addition, the receptor 504 can have characteristic sites that can bind with molecules that are conjugated to the conjugated paramagnetic particles 506. In a particular embodiment, the characteristic site can include biotin and the conjugated paramagnetic particle 506 can be an anti-biotin conjugated paramagnetic particle. In another example, the kit 502 can include another receptor that can bind with the receptor 504 and to which the conjugated paramagnetic particle can bind.

In an exemplary embodiment, the paramagnetic particles 506 are conjugated to a molecule responsive to the receptor 504. For example, the conjugated paramagnetic particles 506 can bind to the receptor 504 when in contact with the receptor 504. In an alternative embodiment, the receptor 504 can be conjugated to the paramagnetic particle 506. The receptor 504 or the conjugated paramagnetic particles 506 can be included in the kit 502 in the form of a lyophilized powder. Alternatively, the receptor 504 or the conjugated paramagnetic particles 506 can be included in the kit 502 as one or more solutions.

The kit 502 optionally can include a paramagnetic particle detector 510. Alternatively, the paramagnetic particle detector 510 can be provided separately. In an exemplary embodiment, the paramagnetic particle detector 510 is configured to determine the amount of conjugated paramagnetic particles 506 associated with the substrate 508. For example, the paramagnetic particle detector 510 can include an antenna or a coil to detect the paramagnetic particle 506. In a particular example, the paramagnetic particle detector 510 can include circuitry configured to determine an influence of the paramagnetic particles on inductance of a sensor and based on the influence, determine a quantity of paramagnetic particles or correlate an amount of the intended target analyte. As described below, the conjugated paramagnetic particles 506 can be subjected to an alternating magnetic field that cause a change in an inductance of a detector inductor of the paramagnetic particle detector 510. The change can cause the oscillation frequency of an oscillator circuit of the paramagnetic particle detector 510 to change. The change in oscillator frequency can be associated by the paramagnetic particle detector 510 with the quantity of conjugated paramagnetic particles 506.

Figure 6:
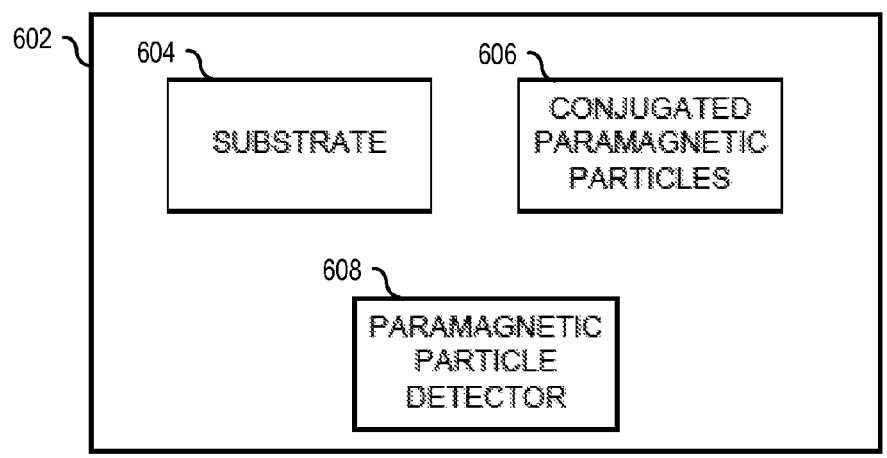

Alternatively, an analyte detection kit can include conjugated paramagnetic particles that bind to an intended target analyte. For example, FIG. 6 is a block diagram illustrating an exemplary analyte detection kit 602. In an exemplary embodiment, the analyte detection kit 602 includes a substrate 604, a conjugated paramagnetic particle 606, and optionally, a paramagnetic particle detector 608. The substrate 604 can include a bound receptor, such as an antibody, reactive to the target analyte. In an example, the substrate 604 is a multi-well plate. Alternatively, the substrate 604 can be a substrate of a semiconductor device.

In an exemplary embodiment, the conjugated paramagnetic particles 606 are reactive to the target analyte or a receptor that is reactive to the target analyte. For example, the conjugated paramagnetic particles 606 can be conjugated to an antibody reactive to the analyte. In an exemplary embodiment, the paramagnetic particle detector 608 is configured to determine the amount of conjugated paramagnetic particles 606 that are associated with the substrate. Alternatively, the paramagnetic particle detector 608 can be provided separately.

Figure 7:
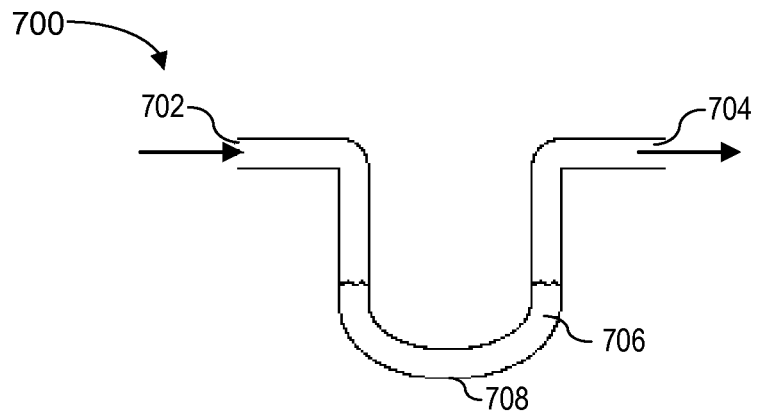
FIGS. 7 and 8 include diagrams illustrating exemplary atmospheric sampling devices.

In addition, a kit can include a sampling mechanism. For example, the kit can include a dropper, a vial, a spoon, tweezers, or any combination thereof. In another exemplary embodiment, the kit can include an atmospheric sampler to acquire samples from air. For example, FIG. 7 and FIG. 8 include illustrations of exemplary atmospheric samplers 700 and 800, respectively. In an example, the atmospheric sampler 700 can include an inlet 702, a trap 708, and an outlet 704. In an embodiment, air can be blown into the inlet 702 and through the trap 708. In another embodiment, air can be vacuumed through the outlet 704, drawing air through the inlet 702 and the trap 708. In a particular example, the trap 708 can include a liquid solution 706 to trap a target analyte. For example, the trap 708 can include water, a saline solution, a solvent, or any combination thereof. In a further example, the solution 706 can include a receptor or conjugated paramagnetic particles. In another example, the trap 708 can be configured to expose a surface of a substrate that includes receptors to the solution 706. For example, the trap 708 can form the substrate or the substrate can be placed in the trap 708. Alternatively, liquid samples can be drawn from the trap 708 and contacted with a substrate.

Figure 8:
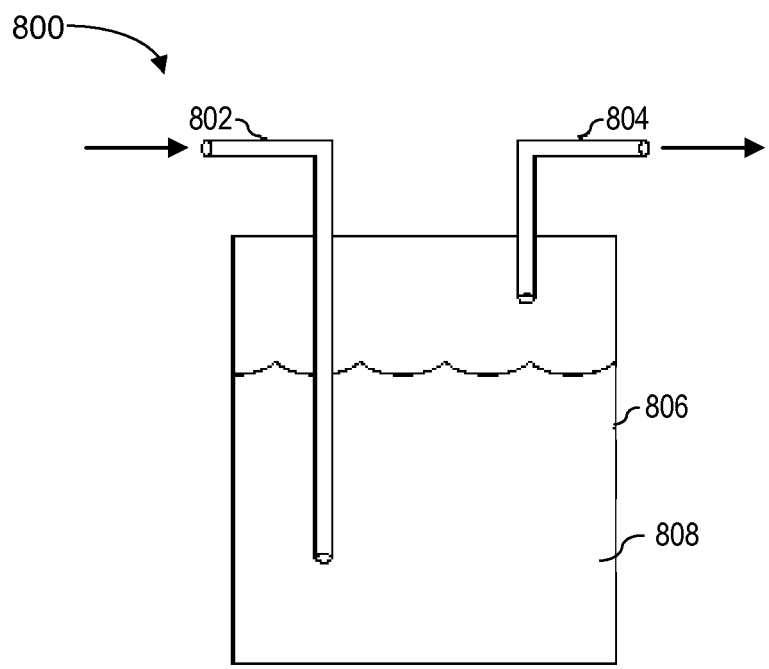

In an alternative example illustrated in FIG. 8, a container or well 806 can be attached to an inlet tube 802 and optionally, an outlet 804. For example, in a closed top system, the container 806 can be attached to an inlet tube 802 and to an outlet tube 804. Atmospheric samples can be blown into the inlet 802 or vacuumed through the outlet 804. In an open top system, the container 806 can be attached to an inlet tub 802 through which an atmospheric sample is blown. The container 806 can include a solution 808 to capture a target analyte. In an additional embodiment, the walls of the container 806, or in particular, the floor of the container 806 can have attached receptors that are responsive to the target analyte. In another embodiment, a substrate having attached receptors can be placed in the container 806. In a further exemplary embodiment, the sample collected in an atmospheric sampler, such as the samplers 700 or 800, can be transferred to a well or applied to a substrate.

Figure 9:
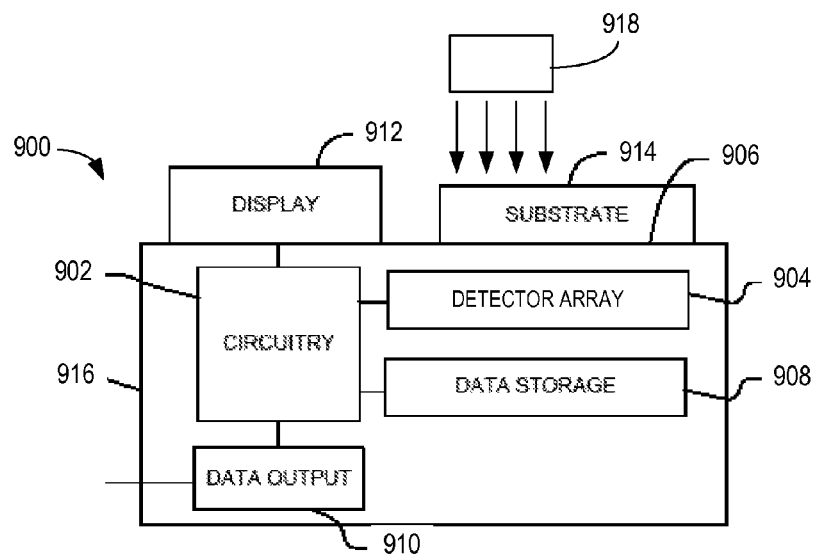
FIG. 9 includes a block diagram illustrating an exemplary analyte detection system.

FIG. 9 includes a block diagram illustrating an exemplary analyte detection system 900. In an exemplary embodiment, the analyte detection system 900 includes a circuitry 902, a detector array 904, and a specimen receiving area 906. The analyte detection system 900 also can include a data storage 908, a data output 910, or a display 912. In a particular example, the circuitry 902, the detector array 904, the data output 910, and the data storage 908 are included in a housing 916. Alternatively, one or more of the circuitry 902, the detector array 904, and the data output 910 or the data storage 908 are included in one or more housings.

The specimen receiving area 906 can be configured to receive a substrate 914 and place the substrate 914 in proximity to the detector array 904. For example, the specimen receiving area 906 can be configured to receive a multi-well plate. In particular, the specimen receiving area 906 can be configured to align a multi-well plate with the detector array 904. For example, the detector array 904 can include more than one antennae, coils, or styluses that can be aligned with wells of the multi-well plate.

The detector array 904 can include more than one antenna that can align with one or more portions of a substrate 914 located in the specimen receiving area 906. The detector array 904 can be coupled to the circuitry 902. The circuitry 902 can manipulate the detector array 904 to determine the influence of a magnetic field on paramagnetic particles. In particular, the circuitry 902 can manipulate each antennae of the detector array 904 to determine the influence of paramagnetic particle in each of the associated wells of the substrate 914. In addition, the paramagnetic particle detector can include a magnetic field generator 918 that can provide a time varying magnetic field in proximity to the substrate 914. In a further example, the detector array 904 can be integrated with the substrate 914 as a unit, and when the unit is in place, the detector array 904 is electrically connected to the circuitry 902.

In an exemplary embodiment, the circuitry 902 includes a set of components that generate an oscillating electromagnetic signal and analyze the generated signal to detect paramagnetic particles. For example, the circuitry 902 can include a set of resistors, transistors, capacitors, or inductors. In an alternative embodiment, the circuitry 902 can include a digital signal processor (DSP) and a direct digital synthesis (DDS) circuit.

In addition, the paramagnetic particle detector 900 can include data storage 908 connected to the circuitry 902. The circuitry 902, for example, can store data on the data storage 908. In addition, the data storage 908 can include parameters and correlations useful by the circuitry 902 to determine the amount of a target analyte. In an example, the data storage 908 can include a hard drive, a removable magnetic media, a removable optical media, a flash media, a random access media, or any combination thereof.

Further, the paramagnetic particle detector 900 can include a data output port 910 coupled to the circuitry 902 to output data. For example, the data output port 910 can be a USB port, a parallel port, a serial port, a network port, or any combination thereof. In a particular example, the data output port 910 can be configured to transmit data to a remote computational system.

In another exemplary embodiment, the paramagnetic particle detector 900 can include a display 912. For example, the display 912 can be coupled to the circuitry 902. The display 912 can be useful for displaying results of tests, configuring the device to detect, or to provide a status of a detection.

Figure 10:
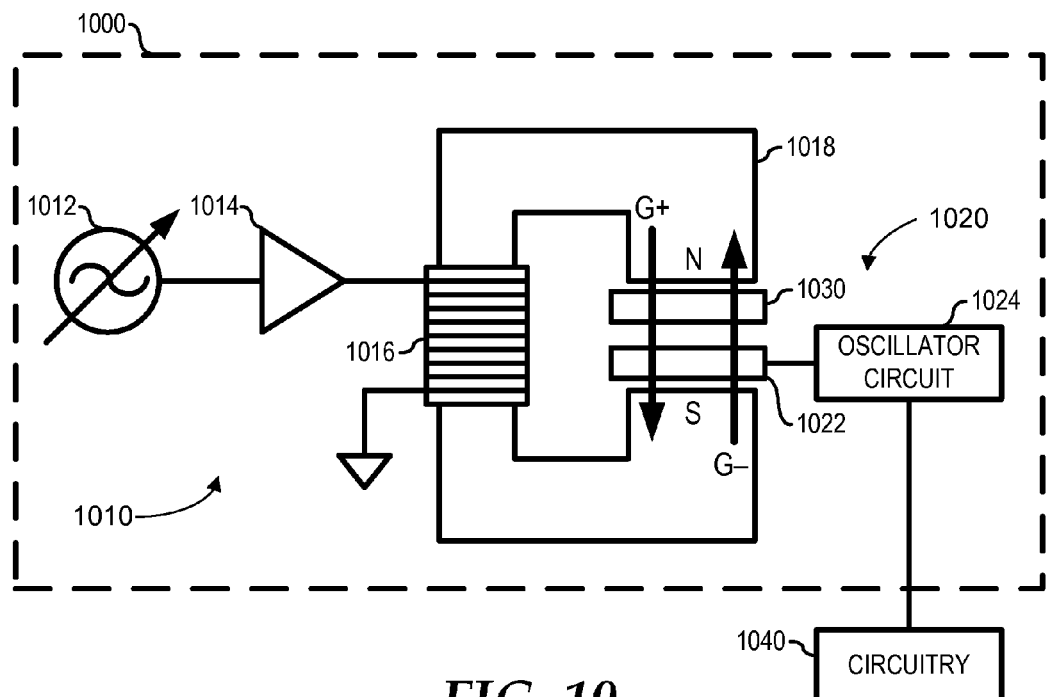
FIG. 10 includes an illustration of an exemplary embodiment of a detector array.

FIG. 10 includes an illustration of an exemplary embodiment of a detector 1000. The detector 1000 includes a magnetic field generator 1010, a detector system 1020, and a specimen receiving area 1030. Detector array 1000 is connected to a circuit 1040. Magnetic field generator 1010 includes a signal generator 1012, a power amplifier 1014, a winding 1016, and a core 1018. The detector system 1020 includes a detector inductor 1022 and an oscillator circuit 1024.

In the illustrated embodiment of the magnetic field generator 1010, the signal generator 1012 is connected to the input of the power amplifier 1014. The output of the power amplifier 1014 is connected to the input of the winding 1016. The output of winding 1016 is connected to a ground terminal. The core 1018 includes two poles, labeled "N" and "S". The winding 1016 is wrapped around a portion of the core 1018. When the signal generator 1012 provides a positive voltage to the winding 1016, a magnetic field, labeled "G+", is induced between the N and S poles of core 1018, and when the signal generator 1012 provides a negative voltage to the winding 1016, an opposite magnetic field, labeled "G−", is induced between the N and S poles of core 1018. In particular, the magnetic field generator 1010 can provide time varying magnetic field, such as an oscillating magnetic field, across a specimen and the detector inductor 1022.

In the illustrated embodiment of the detector system 1020, the detector inductor 1022 is connected to the input of the oscillator circuit 1024, and the output of the oscillator circuit 1024 is connected to the circuitry 1040. The detector inductor 1022 is situated between the N and S poles of the core 1018. In an example, the changing magnetic field induces a time varying voltage signal in the detector inductor 1022, as described below. The voltage signal of the detector inductor 1022 changes the output of the oscillator circuit 1024, and the changing output is detected by the circuitry 1040. In a particular embodiment, the detector inductor 1022 and the oscillator circuit 1024 can form a ring oscillator.

The specimen receiving area 1030 is situated between the N and S poles of the core 1018, and in close proximity to the detector inductor 1022. The specimen receiving area 1030 can be configured to receive a specimen, such as a substrate (not illustrated). The substrate can include an intended target analyte that is bound to conjugated paramagnetic particles. As the amount of conjugated paramagnetic particles changes, as, for example, when the amount of the intended target analyte in one sample is different than the amount of the intended target analyte in another sample, the voltage signal in the detector inductor 1022 changes, which results in different signals in the oscillator circuit 1024, as described below, and can be correlated by the circuitry 1040 to different amounts of the conjugated paramagnetic particles or target analytes.

In an exemplary operation, the magnetic field generator 1010 creates a large magnetic field G in the presence of a substrate to pull the conjugated paramagnetic particles toward the detector inductor 1022. Whether the signal generator 1012 supplies a positive or negative voltage to the winding is determined by the relative magnetic polarity of the conjugated paramagnetic particles.

In a further example, the signal generator 1012 supplies an alternating voltage waveform such that the magnetic field G alternates between G+ and G−, passing through zero magnetic flux at the center of the waveform. The maximum magnitude of G+ and G− is such that the conjugated paramagnetic particles are fully saturated. In an exemplary embodiment, the peak magnetic flux provided by magnetic field generator 1010 can be in the range of 100-500 Gauss (0.01-0.05 Tesla), and the waveform is sinusoidal, and cycles at a rate not greater than 5 MHz, such as in the range of 50-300 Hertz (Hz). In a particular embodiment, the peak magnetic flux can be greater than 300 Gauss (0.03 Tesla) and the waveform cycles at greater than 100 Hz. In particular, a time varying magnetic field can saturate the paramagnetic particles twice per cycle.

The oscillator circuitry 1024 oscillates at a characteristic resonant frequency when there is no specimen or no magnetic field is applied by magnetic field generator 1010. In a particular embodiment, the resonant frequency can be in a range of between 1-500 mega-Hertz (MHz). For example, the resonant frequency can be in a range of 1 to 100 MHz, such as a range of 1 to 50 MHz, a range of 1 to 10 MHz, or even a range of 1 to 5 MHz, when there is not a substrate and no magnetic field is applied by magnetic field generator 1010. When magnetic field generator 1010 is supplying an alternating magnetic field to a specimen, the specimen's moves from saturation to non-saturation state. This alternating condition results from that the fact that paramagnetic specimens have a time-variant magnetic permeability. The time-variant magnetic permeability changes the inductance of the detector inductor 1022 resulting in a time-variant signal which is unique to the specimen. The changed inductance in the detector inductor 1022 results in a change in the resonant frequency of the oscillator circuitry 1024. Thus, the resonant frequency of the oscillator circuitry 1024 varies with a characteristic waveform that can be interpreted by the circuitry 1040.

In the presence of conjugated paramagnetic particles (i.e., when a substrate is present), the conjugated paramagnetic particles become saturated twice in a waveform. The presence of conjugated paramagnetic particles can introduce frequency components in the Bessel sidebands of the signal from the oscillator circuitry 1024.

Thus, the induced voltage in detector inductor 1022 results in a change in the resonant frequency of the oscillator circuitry 1024, but the resonant frequency of the oscillator circuitry 1024 varies with a different waveform than the characteristic waveform, and the different waveform can be interpreted by the circuitry 1040 as indicating the presence of conjugated paramagnetic particles. The degree to which the different waveform differs from the characteristic waveform can be interpreted by the circuitry 1040 as different quantities of conjugated paramagnetic particles. For example, the detector 1020 can be adjusted to zero the frequency component of a sideband in the absence of paramagnetic particles, and the quantity of paramagnetic particles, when present, can be determined based on the amplitude change in the frequency sideband.

Figure 11:
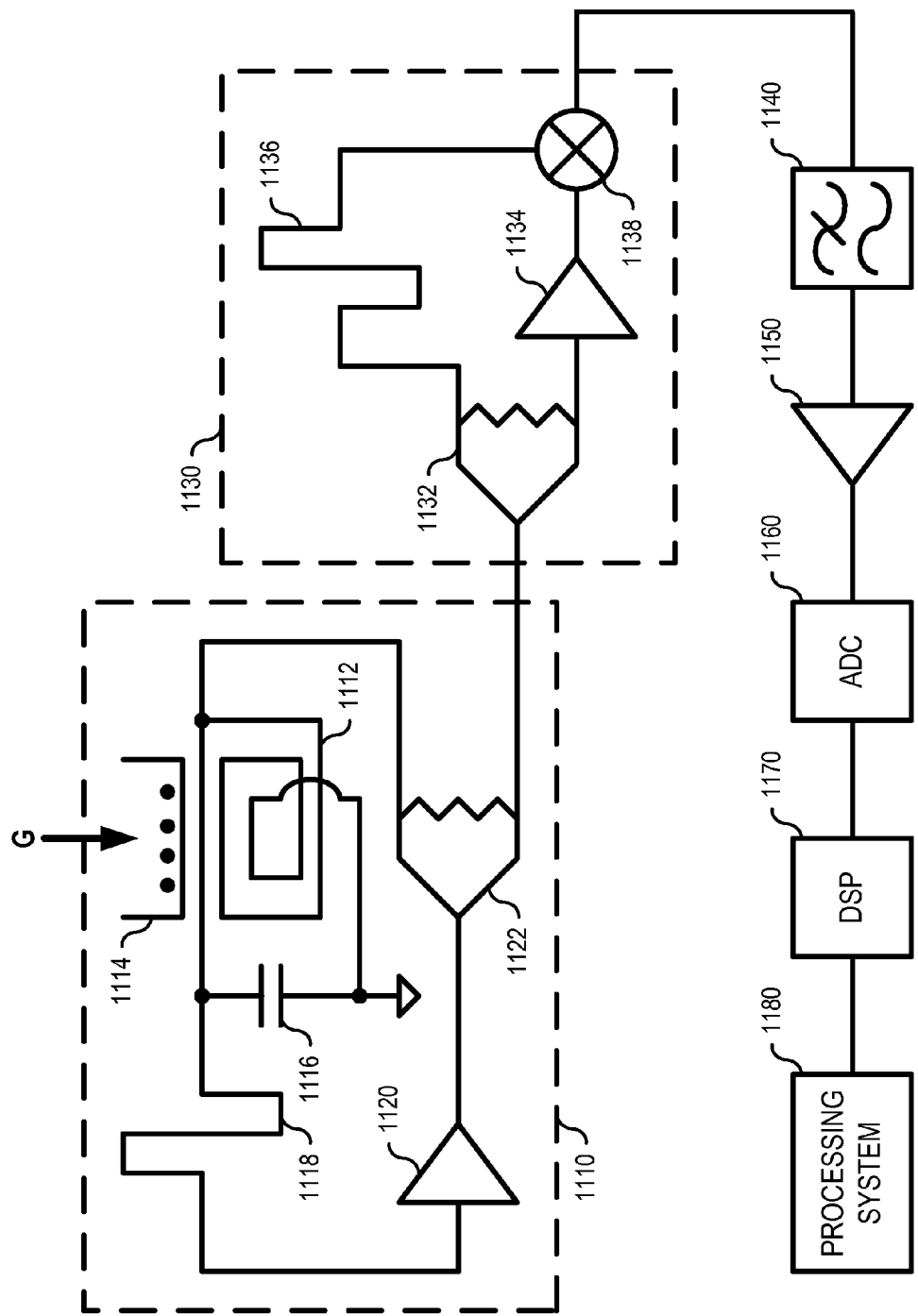
FIG. 11 includes a block diagram illustrating an exemplary embodiment of a detector system.

FIG. 11 includes a block diagram illustrating an exemplary embodiment of a detector system 1100. The detector system 1100 includes a ring oscillator circuit 1110, a discriminator circuit 1130, a low-pass filter (LPF) 1140, a low noise amplifier (LNA) 1150, an analog-to-digital converter (ADC) 1160, a digital signal processor (DSP) 1170, and a processing system 1180. The ring oscillator circuit 1110 has an output connected to an input of the discriminator 1130. The discriminator 1130 has an output connected to an input of the LPF 1140. The LPF 1140 has an output connected to an input of the LNA 1150. The LNA 1150 has an output connected to the input of the ADC 1160. The ADC 1160 has an output connected to an input of the DSP 1170. The DSP 1170 has an output connected to an input of the processing system 1180. The processing system 1180 can include a data storage, a data output, and a display.

The ring oscillator circuit 1110 includes a detector inductor 1112, a specimen receiving area 1114, a capacitor 1116, a delay line 1118, an amplifier 1120, and a power splitter 1122. The detector inductor 1112 has a first terminal connected to a common ground, and a second terminal, and is situated in close proximity to the specimen receiving area 1114. The capacitor 1116 has a first terminal connected to the common ground and has a second terminal connected to the second terminal of the detector inductor 1112. The delay line 1118 has a first terminal connected to the second terminal of the detector inductor 1112 and to the second terminal of the capacitor 1116 and has a second terminal connected to an input terminal of the amplifier 1120. The amplifier 1120 has an output terminal connected to an input terminal of the power splitter 1120. The power splitter 1122 has a first output terminal connected to the second terminal of the detector inductor 1112 and to the second terminal of the capacitor 1116, and a second output terminal operative to provide the output of ring oscillator circuit 1110 and connected to the input of the discriminator 1130.

The discriminator 1130 includes a power splitter 1132, an amplifier 1134, a delay line 1136, and a double balanced mixer (DBM) 1138. The power splitter 1132 has an input operative to provide the input of discriminator 1130 and connected to the output of ring oscillator circuit 1110, a first output terminal connected to an input terminal of the amplifier, and a second output terminal connected to a first terminal of the delay line 1136. The amplifier 1134 has an output terminal connected to a first input terminal of the mixer 1138. The delay line 1136 has a second terminal connected to a second input terminal of the mixer 1138. The mixer 1138 has an output terminal operative to provide the output of the discriminator 1130 and connected to the input of the LPF 1140.

In operation, the detector inductor 1112 and the capacitor 1116 form a parallel resonant filter with a characteristic resonant frequency that is determined by the inductance value of the detector inductor 1112 and the capacitance value of the capacitor 1116. As noted above, in a particular embodiment, the resonant frequency can be between 1-500 MHz, and in an exemplary embodiment, can be between 1 MHz and 100 MHz. In a particular embodiment, the detector inductor 1112 can be a solenoid type inductor with between 10 and 50 turns of wire. In another example, the detector inductor 1112 can be a planar spiral inductor. In an exemplary embodiment the detector inductor 1112 can have greater than 15 turns of wire. In another exemplary embodiment, the detector inductor 1112 can have 20 turns of wire. Each turn of wire can have a nominal area of between 0.25 and 1.0 $cm^2$. In another exemplary embodiment, each turn of wire can have a nominal area of approximately 0.38 $cm^2$. In an exemplary embodiment, a planar spiral detector inductor is constructed on FR4 printed circuit material. In a particular exemplary embodiment, the spiral detector inductor 1112 can be a ¼ inch spiral with between 6-12 rings. In another exemplary embodiment, the spiral detector inductor 1112 can include six rings.

The presence or absence of conjugated paramagnetic particles in the specimen receiving area 1114, and the relative quantity thereof, in the presence of the alternating magnetic field created by a magnetic field generator, changes an inductance of the detector inductor 1112. The inductance causes the resonant frequency of the resonant filter formed by the detector inductor 1112 and the capacitor 1116 to change. The sensitivity of the detector inductor 1112 can be change based upon the location of the specimen receiving area 1030 with respect to the detector inductor 1112. In a particular embodiment, the specimen receiving area 1114 can be centered in the area of the detector inductor 1112. In another embodiment, the specimen receiving area 1114 can be offset from the center of the area of the detector inductor 1112. The sensitivity of the detector inductor 1112 can also be changed based upon the height of the specimen receiving area 1030 above or below the detector inductor 1112. In a particular embodiment, the specimen receiving area 1114 can be directly contacting the detector inductor 1112. In another embodiment, the specimen receiving area 1114 can be between 0.5-15 millimeters (mm), such as between 0.5 mm and 10 mm, between 0.5 mm to 5 mm, or even between 1 mm and 5 mm from the detector inductor 1112. In an exemplary embodiment, the specimen receiving area 1114 can be approximately 3 mm from the detector inductor 1112.

The delay line 1118 is provided to limit low frequency magnetic field induced intermodulation. In a particular embodiment, the delay line 1118 can be implemented with a coaxial line and a mechanical line stretcher. In another embodiment, the delay line 1118 can be replaced with a high pass filter (not illustrated) that can be constructed on FR4 printed circuit material. The delay line 1118 is also provided such that, in combination with the amplifier 1120, the product of the amplifier 1120 gain G, and the feedback loop voltage transfer function H is substantially equal to one. Thus, the ring oscillator circuit 1110 is designed such that the Barkhausen criteria for oscillation are met. The output of the amplifier 1120 is divided into the loop of the ring oscillator circuit 1110 and into the output of the ring oscillator circuit 1110. In a particular embodiment, the power divider 1122 is a resistive divider with six decibels (dB) of insertion loss.

In operation, the discriminator 1130 functions to convert the changing frequency output from ring oscillator circuit 1110 into a corresponding change in a voltage signal. The input of the discriminator 1130 is divided into two paths by power divider 1132. The first path is through the amplifier 1132 to the mixer 1138. In a particular embodiment, the power divider 1132 is a torroidal hybrid divider with three dB of insertion loss. The discriminator 1130 can be optimized for linear dynamic range by using a high-level output, low distortion amplifier for the amplifier 1134. In a particular embodiment, the amplifier 1134 can provide 13 dB of gain. The output of the amplifier 1134 is fed to the local oscillator (LO) input of the mixer 1138. The second path from the power divider 1132 is through the delay line 1136 to the mixer radio frequency (RF) input of the mixer 1138.

The output of the LPF 1140 is amplified in the LNA 1150, and the voltage signal is digitized in the ADC 1160. The digitized signal is passed through the DSP 1170. The DSP 1170 can include a digital Fast Fourier Transform, and the resulting signals can be analyzed by the processing system 1180 to provide a measure of the quantity of the conjugated paramagnetic particles in a sample. In a particular embodiment, the processing system 1180 can be a general purpose processing system such as a personal computer, a laptop computer, or a mobile computing device. The processing system can also function to interpret the quantity of conjugated paramagnetic particles in terms of a concentration of the associated analyte.

Figure 12:
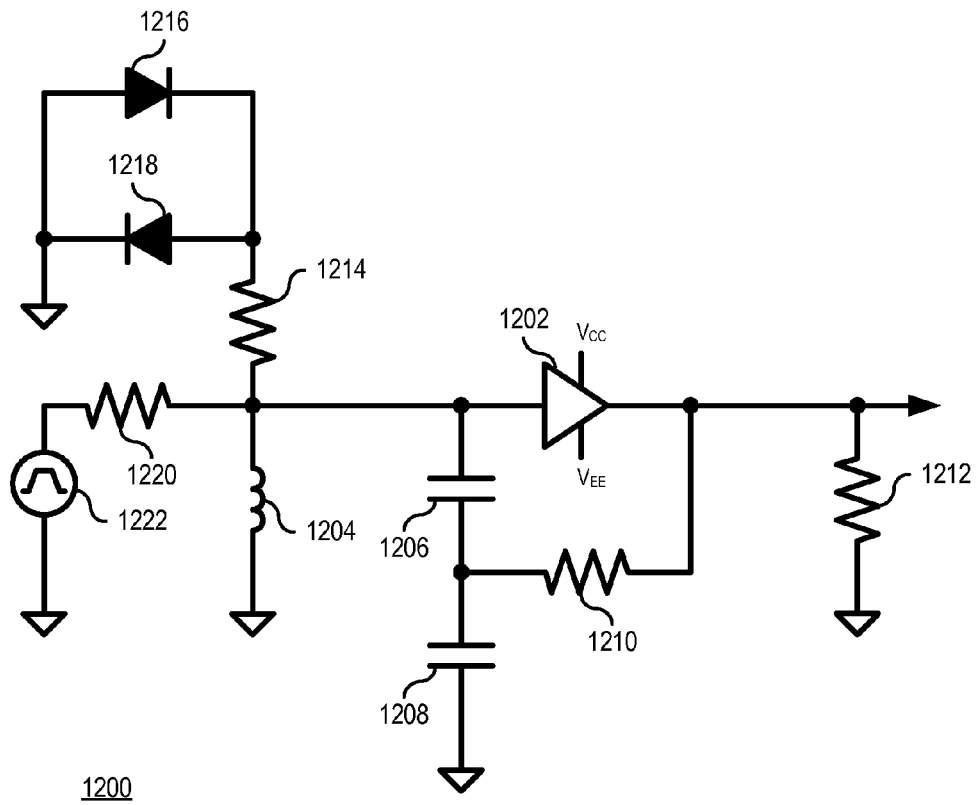
FIG. 12 includes a schematic diagram illustrating an exemplary amplifier circuit that provides linear gain and amplitude limiting.

In a particular embodiment, the detection system 1100 can be improved by improving the linearity of the oscillator circuit 1110, and by limiting the amplitude of the oscillations. Various alternative oscillator circuits can be used, including vacuum tube-containing oscillators or JFET Colpits oscillators, among others. While various amplifiers having desirable linearity can suffice, FIG. 12 is a schematic diagram illustrating an exemplary circuit 1200 that provides desirable linear gain and amplitude limiting. The circuit 1200 includes an amplifier integrated circuit (IC) 1202, a detector inductor 1204, capacitors 1206 and 1208, resistors 1210, 1212, 1214, and 1220, diodes 1216 and 1218, and a signal generator 1222.

The amplifier IC 1202 has an input terminal, an output terminal, a positive voltage supply terminal labeled "$V_{CC}$", and a negative voltage supply terminal labeled "$V_{EE}$". The detector inductor 1204 has a first terminal connected to the input terminal of the amplifier IC 1202 and has a second terminal connected to a common ground terminal. The capacitor 1206 has a first terminal connected to the input terminal of the amplifier IC 1202 and has a second terminal. The capacitor 1208 has a first terminal connected to the second terminal of the capacitor 1206 and has a second terminal connected to the common ground. The resistor 1210 has a first terminal connected to the second terminal of the capacitor 1206 and has a second terminal connected to the output terminal of the amplifier IC 1202. The resistor 1212 has a first terminal connected to the output terminal of the amplifier IC 1202 and has a second terminal connected to the common ground. The resistor 1214 has a first terminal connected to the input terminal of the amplifier IC 1202 and has a second terminal. The diode 1216 has an anode terminal connected to the common ground and has a cathode terminal connected to the second terminal of the resistor 1214. The diode 1218 has an anode terminal connected to the second terminal of the resistor 1214 and has a cathode terminal connected to the common ground. The resistor 1220 has a first terminal connected to the input terminal of the amplifier IC 1202 and has a second terminal connected to a first terminal of the signal generator 1222. The signal generator 1222 has a second terminal connected to the common ground.

In a particular embodiment, the amplifier IC 1202 has a bandwidth that is approximately 20 times the frequency of oscillation so that the amplifier IC 1202 does not introduce unwanted phase shift or frequency distortion. In a particular embodiment, the amplifier IC 1202 is implemented with a National Semiconductor CLC111—Ultra High Slew Rate, Closed Loop Buffer. The amplifier IC 1202 provides amplitude limiting as a function of the voltage supplies. Additional amplitude limiting is provided by diodes 1216 and 1218. Additional linearization and reduced slew rate are provided by the resistor 1210.

Figure 14:
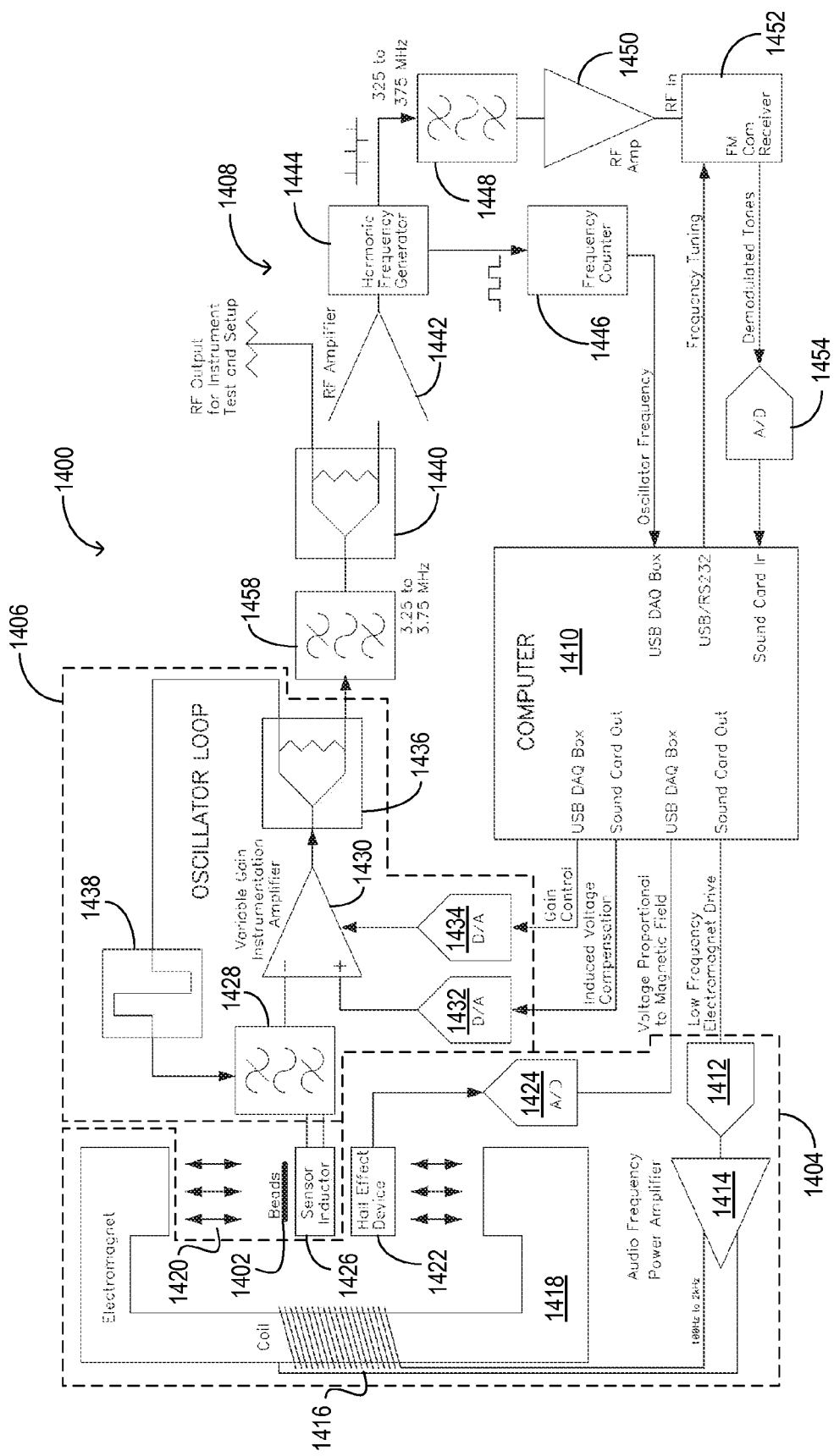
FIG. 14 includes a schematic diagram illustrating an exemplary detection circuitry.

In another embodiment illustrate in FIG. 14, the influence of a specimen, such as paramagnetic beads 1402, on a time varying magnetic field 1420 is measured by a sensor inductor 1426. The system 1400 includes a field generation circuitry 1404 to generate the time varying magnetic field 1420. In addition, the system 1400 includes the sensor inductor 1426 connected to and forming part of an oscillator loop 1406 which is connected to analysis circuitry 1408, such as a demodulation circuitry. Each of the circuitries 1404, 1406, and 1408 can be connected to a computational system 1410 to control the behavior of the circuitry and to further process the output.

In a particular example, the computational circuitry 1410 provides an electromagnetic drive signal to the field generation circuitry 1404. For example, the electromagnetic drive signal can be provided to a digital-to-analog converter 1412 that is coupled to an amplifier 1414. The amplifier 1414 provides current to a coil 1416 wrapped around a column of the electromagnet 1418, such as a C-shaped electromagnet. As a result, the electromagnetic drive signal is converted into a time varying magnetic field 1420. In an example, the time varying magnetic field 1420 has a frequency of not greater than 5 $MH_Z$. For example, the frequency can be not greater than 1 MHz, such as not greater than 500 kHz, not great greater than 100 kHz, or even not greater than 1 kHz. In an example, the time varying magnetic field 1420 has a frequency in a range of 50 to 1000 hertz, such as a range of 50 to 500 hertz, or even a range of 50 to 250 hertz. Alternatively, the time varying magnetic field 1420 can have a frequency in a range of 500 hertz to 100 kHz, such as a range of 1 kHz to 100 kHz, or even a range of 10 kHz to 80 kHz.

In an example, the inductance presented to the amplifier 1414 can be at low frequencies. Optionally, the amplifier can be provided with an additional load to limit current wave form distortion. Resisters can be placed in series with the electromagnetic coil, such as 6 ohms of resistance to provide a load to an 8 ohm output impedance power amplifier.

Optionally, the frequency generation circuitry 1404 can include a Hall Effect device 1422 to assist with measuring and tuning the time varying magnetic field 1420. For example, the Hall Effect device 1422 can be connected to the computer 1410 via an analog-to-digital converter 1424. When tuning the time varying electromagnetic field 1420, the Hall Effect device 1422 can be placed between the arms of the electromagnet 1418. The time varying magnetic field 1420 is detected and measured by its influence on the Hall Effect device 1422. With the measurements from the Hall Effect device 1422, the computer 1410 can be used to tune the time varying magnetic field 1420 by manipulating the electromagnetic drive signal. Optionally, the Hall Effect device 1422 can be removed from between the arms of the electromagnet 1418 once the time varying magnetic field 1420 is measured or tuned.

To quantify or analyze a specimen, such as the beads 1402, a specimen and a sensor inductor 1426 are placed into the time varying magnetic field 1420 between the poles of the electromagnet 1418. In an example, a well plate supporting the specimen and the sensor inductor can be formed as a single integral unit or can be separate components. The sensor inductor 1426 is connected to an oscillator loop 1406, which in turn is connected to analysis circuitry 1408. In an example, the sensor inductor 1426 is DC isolated from the amplifier components through the use of an oscillator loop 1406 instead of a negative impedance for L/C feedback. The oscillator loop 1406 can also permit external gain control that limits the non-linearities of amplifier saturation and permit nulling the anti-phase signals that can be used to limit harmonics and intermodulation products within the oscillator loop.

In a particular example, the oscillator loop 1406 includes a band pass filter 1428 connected to an amplified 1430, the output of which is connected to a divider 1436. A portion of the output from the amplifier 1430 is fed back to the band pass filter 1428 via the divider 1436. Optionally, the system can include a delay line 1438 in the feedback from the divider 1436. In particular, delay line 1438 can be used if the loop phase shift differs from approximately 360°, a condition for oscillation to occur according to Barkhausen criterion. The band pass filter 1428 is coupled to the sensor inductor 1426 and can provide DC isolation to the sensor inductor 1426. The sensor inductor 1426 is the primary frequency/phase determining element of the band pass filter 1428. The band pass filter 1428 also provides an impedance transformation so that the Q of the inductor is maximized in the low impedance circuit. For example, the low impedance circuit can have a characteristic impedance of approximately 50 ohms.

The amplifier 1430 can be a variable gain amplifier that permits reducing loop gain to the extent that the loop oscillates but does not go into deep saturation. As a result, the amplifier 1430 can reduce intermodulation components in a resulting signal that result from inductor induced voltage mixing with oscillation voltage when the amplifier approaches saturation. In a particular example, the computational circuitry 1410 can provide gain control through digital-to-analog converter 1434 into the amplifier 1430. In addition, the computational circuitry 1410 can provide an induced voltage compensation through a digital-to-analog converter 1432 connected to the positive pole of the amplifier 1430. In such a manner, desired parameters of operation can be provided to the oscillator loop 1406. For example, such parameters are provided prior to measuring or detecting the influence of the specimen on the time varying magnetic field 1420. When the specimen is being measured, the control parameters provided to the oscillation loop 1406 can be held constant to prevent further influence of the control parameters on the measured signal.

As stated above, the output from the oscillation loop 1406 is provided to an analysis circuitry 1408. For example, a portion of the output from divider 1436 can be provided into a band pass filter 1458. The band pass filter 1458 is connected to a distributor 1440 and a portion of the output from the distributor 1440 is applied to an amplifier 1442. Another portion of the output from the distributor 1440 can be provided to instrumentation for testing and setup of the circuitry. During normal operation, the output can not be used and can be terminated with a 50 ohm load.

The output from the amplifier 1442 is provided to a harmonic frequency generator 1444. Output from the harmonic frequency generator 1444 can be provided to a frequency counter 1446 and another output can be provided to a band pass filter 1448. The frequency counter 1446 can provide frequency data to the computational circuitry 1410.

The output from the band pass filter 1448 can be applied to the amplifier 1450, which in turn provides output to the receiver 1452. The receiver 1452 can provide demodulated tones to the computational circuitry, such as via an analog-to-digital converter 1454. In a particular example, the receiver 1452 can receive a frequency tuning from the computational circuitry 1410.

Returning to the band pass filter 1458, the harmonics of the fundamental oscillator frequency can be attenuated absent the band pass filter 1458. It was found that further non-linearities can be produced by the harmonic frequency generator 1444, which cause vector summoning of the oscillator generated harmonics and the frequency multiplier harmonics that can change the level of the side bands generated by the specimen in the various magnetic field.

In an example, the harmonic frequency generator 1444 is a combination of squaring and fast rise time gates. In an example, an output is taken from the squaring circuit to be counted by the counter 1446. Such counting gives the operation frequency for the receiver. It is preferred that the oscillator frequency not be tuned during a measurement. The frequency is determined by the sensor inductor 1426. Optionally, the receiver frequency can be dynamically tuned either by computer or with an automatic frequency control.

Harmonics used for the analysis can be limited by the band pass filter 1448, which receives outputs from fast rise time gates of the harmonic frequency generator 1444. In an example, the $100^{th}$ harmonic of the oscillator fundamental can provide reasonable multiplication of the phase shift caused by the specimen and the magnetic field variation. In a particular example, filtering the harmonic spectrum before it is applied to the demodulation receiver reduces inter-harmonic generation in the sensitive front end circuits of the receiver. In a particular example, to increase measurement options, the filter 1448 can be a 3-section high pass filter cutting off at about 100 MHz. Such a filter an attenuate the large harmonic components below 100 MHz and passes everything above, depending upon the receiver front end filter to reduce unwanted spectral components. As a result, harmonic numbers from 1 to over 150 can be used.

Because a small amount of phase modulation introduced by the specimen and the varying magnetic field has been multiplied by the harmonic number to the harmonic frequency generator output, the frequency modulated signal can be detected in an FM receiver, such as the receiver 1452. In an example, the frequency of the primary oscillation is determined by the frequency counter 1446 and the receiver 1452 is tuned to "N" times the primary frequency the number. Such tuning can be performed manually or can be automated. The resulting demodulated tones can be provided to the computational circuitry 1410 via the analog-to-digital converter 1454.

In a particular embodiment, the system 1400 can be implemented with a computational circuitry 1410, such as a laptop connected to a measurements computing mini-lab. The laptop computer can run control measurement software implemented in Visual Basic or Visual-C or available commercially as National Instruments DasyLab. Further, the computation circuitry can be implemented as one or more computers, such as PC computers.

Figure 13:
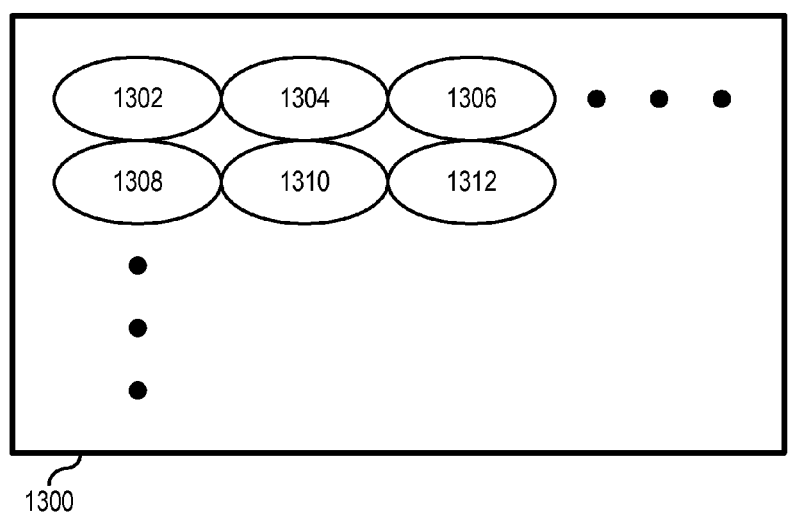
FIG. 13 includes an illustration of an exemplary arrangement of an array of detectors.

In a particular embodiment, the array of detectors is configured to measure conjugated paramagnetic particles in an array of locations on a substrate. For example, the substrate can be a multi-well plate. In particular, the array can include at least four detectors in an arrangement wherein at least one detector of the at least four detectors is adjacent to at least three other detectors of the at least four detectors. For example, FIG. 13 is a diagram illustrating an exemplary arrangement 1300. The arrangement can include at least 4 positions. As illustrated, the arrangement 1300 includes at least 6 positions 1302, 1304, 1306, 1308, 1310, and 1312. As illustrated, there can be additional positions extending the arrangement of rows and columns. In a particular example, the rows and columns extend in a ratio of two rows to three columns. For example, the array can include at least about 48 positions. In another example, the array can include at least about 96 positions. In a further example, the array can include at least about 384 positions, such as at least about 1536 positions.

Further, any two adjacent positions can have center points that are not greater than 2 cm apart. For example, two positions can have center points that are not greater than 1.5 cm apart.

In an exemplary embodiment, the position 1302 is adjacent three other positions 1304, 1308, and 1310 and the position 1304 is adjacent to the other positions, 1302, 1306, 1308, 1310, and 1312. In a further example, the position 1310 can be adjacent to at least 5 other positions, such as 8 positions.

In an exemplary embodiment, the arrangement can align with the arrangement of at least a portion of positions of a substrate. For example, the array can be configured to align the antennae with a set of wells in a multi-well substrate. In a particular example, the substrate can include at least four wells in an arrangement wherein at least one well of the at least four wells is adjacent to at least three other wells of the at least four wells. As such, the positions illustrated in FIG. 13 can correspond to positions on a substrate. In particular, there can be additional wells extending the arrangement of rows and columns. For example, the rows and columns can extend in a ratio of two rows to three columns. In a particular example, the substrate can include at least about 48 wells. In another example, the substrate can include at least about 96 wells. In a further example, the substrate can include at least about 384 wells, such as at least about 1536 wells. Further, any two adjacent wells can have center points that are not greater than 2 cm apart, such as not greater than 1.5 cm apart.

Where a substrate includes multiple positions, the magnetic field generator can be implemented as a single magnetic field generator that provides the magnetic field G to all of the multiple positions of the substrate. In another embodiment, the magnetic field generator can be implemented as multiple magnetic field generators.

EXAMPLES

Test samples having various numbers of paramagnetic beads are measured using the circuitry illustrated in FIG. 14. The Hall Effect sensor is placed within the electromagnetic field area and the desired magnetic field frequency is set, such as a frequency of around 200 hertz. The magnitude of the field is set for about 500 Gauss, O-peak. Such a field generally is enough to saturate iron oxide contained in the beads used for testing.

The drive generator, implemented in software in a computer laptop, produces fundamental drive frequencies and additional signals up to four times the fundamental frequency. The additional signals are summed with variable drive levels to (1) predistort the magnetic drive current to reduce harmonic frequency content in the magnetic field and (2) provide nulling signals to the oscillator loop to reduce sensitivity limiting harmonic output from the oscillator. A Measurement Computing Mini-Lab 1008 is used to provide data access. The computer, under control of counter software, zeroes the counter and produces a strobe pulse to the grading circuit on a printed circuit board including the circuitry components. The resulting crystal controlled dating signal passes the test oscillator output to the event counter for a very precise period of time. The counter counts the zero crossings and the software computes the frequency of the oscillator. The system can determine the frequency to which the communications receiver is to be tuned or such a frequency can be set manually based on visually inspected output from the counter.

Once the system magnetic field and frequency harmonic numbers have been set, manual harmonic balancing of oscillator distortion products and measurement of the relative magnitude of the sidebands induced by saturating paramagnetic beads can be performed.

In a particular example, using a magnetic field frequency of 200 Hertz and the $10^{th}$ harmonic of the sensor oscillator (normally 35 MHz), it is possible to iteratively reduce the harmonic at 400 hertz to the noise level within the generator screen controls on a computer.

Specimens are prepared in a decade count sequence (670 k, 67 k and 6.7 k) with cellophane tape holders to facilitate convenient insertion and removal into the inductor platform. In particular, the sample is placed at the 3-dimensional geometric center of the coil. The data reported is for the sample sitting on top of the coil, not within the coil. Inserting a first specimen having 670 k beads into the magnetic field just above the sensing inductor results in an increase of the 400 hertz component to 20 dB above the noise. The signal is strong and steady with the variance on the input being due to time required to position the sample. A second specimen with 67 k beads produces a 3-dB increase in the 400 hertz component, and a third sample having 6.7 k beads produces an increase of less than 1 dB in the 400 hertz component.

By increasing harmonic number, sensitivity can be improved. In addition automatic nulling of harmonic components in the oscillator can facilitate real time measurement without the attendant drift problems of a manual system, improving precision higher harmonic measurements. In addition, improvement in analog-to-digital and digital-to-analog converters, as well as other components can improve the detection threshold of the system.

In a first embodiment, a detection system includes an oscillator circuit including an inductive sensor. The inductive sensor is in proximity to a specimen exposed to a time varying magnetic field. The detection system also includes an analysis circuitry to receive a signal from the oscillator circuitry.

In an example of the first embodiment, the specimen is paramagnetic.

In another example of the first embodiment, the detection system further includes a field generation circuit to generate the time varying magnetic field.

In an additional example of the first embodiment, the oscillator circuit further includes an amplifier and a splitter coupled to an output of the splitter. The oscillator circuit can further include a band pass filter. A portion of the output of the splitter is provided to an input of the band pass filter. The inductive sensor is connected to the band pass filter. An output of the band pass filter is connected to an input of the amplifier.

In a further example of the first embodiment, the analysis circuit includes a harmonic frequency generator to receive a signal from the oscillator circuit and includes a radio frequency receiver to receive a signal from the harmonic frequency generator. The detection system can further include a band pass filter coupled in series between the harmonic frequency generator and the radio frequency receiver. The detection system can further include a counter to receive a signal from the harmonic frequency generator.

In a second embodiment, an analyte detection system includes a first detector configured to be situated in close proximity to a first well of a substrate. The first well to include a first quantity of conjugated paramagnetic beads. The analyte detection system further includes a magnetic field generator operable to provide an oscillating magnetic field in the first well and in the first detector, a first oscillator circuit coupled to the first detector and having a first output, and a circuitry coupled to the first output, and operable to determine the first quantity of conjugated paramagnetic beads.

In an example of the second embodiment, the magnetic field generator is operable to provide the oscillating magnetic field at a magnetic field strength that magnetically saturates the first quantity of conjugated paramagnetic beads. The magnetic field strength can be between 100 and 500 Gauss, such as the magnetic field strength can be greater than 300 Gauss.

In another example of the second embodiment, a frequency of oscillation of the oscillating magnetic field is between 50 and 500 mega-Hertz. For example, a frequency of oscillation of the oscillating magnetic field is 100 mega-Hertz.

In a further example of the second embodiment, the first detector includes an inductor. In an example, the inductor includes a planar inductor in a spiral configuration to include between six and twelve loops. For example, the spiral planar inductor includes six loops. In a further example, the planar inductor is constructed on a printed circuit board. In another example, the first oscillator circuit includes a ring oscillator. For example, the first oscillator circuit output can include a signal corresponding to the oscillating magnetic field. In a particular example, the signal includes a first signal characteristic when the first quantity of conjugated paramagnetic beads is equal to zero conjugated paramagnetic beads and a second signal characteristic when the first quantity of conjugated paramagnetic beads is not equal to zero conjugated paramagnetic beads. In an example, the circuitry is further operable to distinguish between the first signal characteristic and the second signal characteristic, associate the first signal characteristic with a zero quantity of conjugated paramagnetic beads, and associate the second signal characteristic with a non-zero quantity of conjugated paramagnetic beads. For example, the circuitry includes a phase discriminator. In another example, the circuitry further comprises a processing system. For example, the processing system comprises a computer.

In an additional example of the second embodiment, the analyte detection system further includes a second detector configured to be situated in close proximity to a second well of a substrate, the second well to include a second quantity of conjugated paramagnetic beads, and a second oscillator circuit coupled to the second detector and having a second output. The magnetic field generator is further operable to provide the oscillating magnetic field in the second well and the circuitry is further coupled to the second output, and further operable to detect the second quantity of conjugated paramagnetic beads.

In a third embodiment, a method of detecting analytes includes applying a magnetic field to well of a substrate, the well to include a quantity of conjugated paramagnetic beads, alternating a polarity of the magnetic field between a positive polarity and a negative polarity, detecting a characteristic signal associated with the alternating magnetic field, and associating the characteristic signal with the quantity of conjugated paramagnetic beads.

In an example of the third embodiment, the alternating magnetic field has a magnetic field strength that magnetically saturates the first quantity of conjugated paramagnetic beads.

In another example of the third embodiment, the magnetic field strength is between 100 and 500 Gauss. In an additional example, the magnetic field strength is greater than 300 Gauss.

In a further example of the third embodiment, a frequency of oscillation of the alternating magnetic field is between 50 and 500 mega-Hertz. In an example, a frequency of oscillation of the alternating magnetic field is 100 mega-Hertz.

In an additional example of the third embodiment, detecting the characteristic signal includes inducing a voltage change in an inductor. For example, detecting the characteristic signal further includes changing an oscillation frequency of an oscillator circuit based upon the induced voltage change in the inductor. In another example, associating the characteristic signal with the quantity of conjugated paramagnetic beads includes detecting a phase change in the oscillation frequency of the oscillator circuit. In an additional example, associating the characteristic signal with the quantity of conjugated paramagnetic beads further includes detecting a phase change in the oscillation frequency and associating the detected phase change with the quantity of conjugated paramagnetic beads.

In a fourth embodiment, an analyte detection kit includes a substrate having an antibody attached to the substrate, the antibody being reactive to the analyte, a conjugated paramagnetic particle, and a conjugated paramagnetic particle detector. The particle detector includes a detector configured to be situated in close proximity to a well of the substrate, the well to include the conjugated paramagnetic particle, a magnetic field generator operable to provide an oscillating magnetic field in the well and in the detector, a oscillator circuit coupled to the detector and having an output, and a circuitry coupled to the output, and operable to detect the conjugated paramagnetic particle.

In an example of the fourth embodiment, the magnetic field generator is operable to provide the oscillating magnetic field at a magnetic field strength that magnetically saturates the conjugated paramagnetic particle. In a further example, the magnetic field strength is between 100 and 500 Gauss and a frequency of oscillation of the oscillating magnetic field is between 50 and 500 mega-Hertz. In an additional example, the magnetic field strength is greater than 300 Gauss and a frequency of oscillation of the oscillating magnetic field is 100 mega-Hertz.

In another example, the detector includes an inductor and the oscillator circuit comprises a ring oscillator. For example, the oscillator circuit output comprises a signal corresponding to the oscillating magnetic field. The signal includes a first waveform when the conjugated paramagnetic particle is not present and a second waveform when the conjugated paramagnetic particle is present. In an additional example, the circuitry is further operable to distinguish between the first waveform and the second waveform, associate the first waveform with the absence of the conjugated paramagnetic particle, and associate the second waveform with the presence of the conjugated paramagnetic particle.

Note that not all of the activities described above in the general description or the examples are required, that a portion of a specific activity can not be required, and that one or more further activities can be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. An analyte detection system comprising:
a first detector configured to be situated in proximity to a first well of a substrate, the first well to include a first quantity of conjugated paramagnetic beads, the first detector including an inductive sensor;
a magnetic field generator operable to provide an oscillating magnetic field in the first well and in the first detector;
a first oscillator circuit including an oscillator loop and having a first output, the oscillator loop including a bandpass filter coupled to an amplifier coupled to a signal divider with feedback to the bandpass filter, the signal divider providing the first output, the inductive sensor connected to the bandpass filter of the oscillator loop to cause a change in a frequency or phase of a signal at the signal divider responsive to the first quantity of conjugated paramagnetic beads in the presence of the oscillating magnetic field; and
a circuitry coupled to the first output and operable to determine the first quantity of conjugated paramagnetic beads, the circuitry including a harmonic frequency generator to receive a signal from the signal divider and including a receiver to demodulate a frequency signal generated by the harmonic frequency generator to provide a tone indicative of the first quantity of conjugated paramagnetic beads.

2. The analyte detection system of claim 1, wherein the magnetic field generator is operable to provide the oscillating magnetic field at a magnetic field strength that magnetically saturates the first quantity of conjugated paramagnetic beads.

3. The analyte detection system of claim 2, wherein the magnetic field strength is between 100 and 500 Gauss.

4. The analyte detection system of claim 2, wherein a frequency of oscillation of the oscillating magnetic field is between 50 and 500 Hertz.

5. The analyte detection system of claim 1, wherein the inductive sensor comprises a planar inductor in a spiral configuration to include between six and twelve loops.

6. The analyte detection system of claim 1, wherein the first oscillator circuit comprises a ring oscillator.

7. The analyte detection system of claim 1, wherein the signal comprises:
a first signal characteristic when the first quantity of conjugated paramagnetic beads is equal to zero conjugated paramagnetic beads; and
a second signal characteristic when the first quantity of conjugated paramagnetic beads is not equal to zero conjugated paramagnetic beads.

8. The analyte detection system of claim 7, wherein the circuitry is further operable to:
distinguish between the first signal characteristic and the second signal characteristic;
associate the first signal characteristic with a zero quantity of conjugated paramagnetic beads; and
associate the second signal characteristic with a non-zero quantity of conjugated paramagnetic beads.

9. The analyte detection system of claim 8, wherein the circuitry comprises a phase discriminator.

10. The analyte detection system of claim 1, further comprising:
a second detector configured to be situated in proximity to a second well of a substrate, the second well to include a second quantity of conjugated paramagnetic beads; and
a second oscillator circuit coupled to the second detector and having a second output; and
wherein:
the magnetic field generator is further operable to provide the oscillating magnetic field in the second well; and
the circuitry is further coupled to the second output, and further operable to detect the second quantity of conjugated paramagnetic beads.

11. The analyte detection system of claim 1, further comprising a delay line in communication between the signal divider and the band pass filter.

12. The analyte detection system of claim 1, wherein the inductive sensor is coupled to the band pass filter.

13. The analyte detection system of claim 12, wherein the inductive sensor is a frequency/phase determining element of the band pass filter.

14. The analyte detection system of claim 1, wherein the amplifier is a variable gain amplifier.

15. The analyte detection system of claim 1, wherein the output of the first oscillator circuit is connected to a band pass filter and an output of the band pass filter is connected to a second amplifier.

16. The analyte detection system of claim 15, wherein an output of the second amplifier is connected to the harmonic frequency generator.

17. The analyte detection system of claim 1, further comprising a band pass filter coupled in series between the harmonic frequency generator and the receiver, the receiver comprising a radio frequency receiver.

18. The analyte detection system of claim 17, further comprising a frequency counter to receive a counting signal from the harmonic frequency generator and to provide a frequency to tune the receiver.

19. The analyte detection system of claim 1, wherein the oscillator loop operates at a frequency different from the oscillating magnetic field.

* * * * *